United States Patent
Thayumanavan et al.

(10) Patent No.: US 10,617,652 B2
(45) Date of Patent: Apr. 14, 2020

(54) POLYMERS AND POLYMERIC NANOGELS WITH HYDROPHILICS ENCAPSULATION AND RELEASE CAPABILITIES AND METHODS THEREOF

(71) Applicant: University of Massachusetts, Boston, MA (US)

(72) Inventors: Sankaran Thayumanavan, Amherst, MA (US); Mijanur Rahaman Molla, Amherst, MA (US); Scott Clayton Garman, Amherst, MA (US)

(73) Assignee: University of Massachusetts, Boston, MA (US)

( * ) Notice: Subject to any disclaimer, the term of this patent is extended or adjusted under 35 U.S.C. 154(b) by 23 days.

(21) Appl. No.: 15/508,955

(22) PCT Filed: Sep. 17, 2015

(86) PCT No.: PCT/US2015/050810
§ 371 (c)(1),
(2) Date: Mar. 6, 2017

(87) PCT Pub. No.: WO2016/044663
PCT Pub. Date: Mar. 24, 2016

(65) Prior Publication Data
US 2017/0333363 A1    Nov. 23, 2017

Related U.S. Application Data

(60) Provisional application No. 62/051,887, filed on Sep. 17, 2014.

(51) Int. Cl.
*A61K 9/51* (2006.01)
*A61K 9/06* (2006.01)
*A61K 47/34* (2017.01)
*A61K 9/107* (2006.01)
*C12N 15/11* (2006.01)
*A61K 31/713* (2006.01)
*C08F 120/28* (2006.01)

(52) U.S. Cl.
CPC .............. *A61K 9/5138* (2013.01); *A61K 9/06* (2013.01); *A61K 9/1075* (2013.01); *A61K 31/713* (2013.01); *A61K 47/34* (2013.01); *C08F 120/28* (2013.01); *C12N 15/111* (2013.01); *C12N 2310/11* (2013.01); *C12N 2310/14* (2013.01); *C12N 2310/16* (2013.01); *C12N 2320/32* (2013.01)

(58) Field of Classification Search
None
See application file for complete search history.

(56) References Cited

PUBLICATIONS

Zhaung et al. Dual Stimuli—Dual Response Nanoassemblies Prepared from a Simple Homopolymer ACS Macro Lett, 2014, 21, 3(1) : pp. 1-5 (Year: 2014).*
(Continued)

*Primary Examiner* — Robert A Wax
*Assistant Examiner* — Melissa S Mercier
(74) *Attorney, Agent, or Firm* — Milstein Zhang & Wu LLC

(57) ABSTRACT

The invention provides pH- or redox-responsive and charge-neutral polymeric nanogels that stably encapsulate a biomolecule at one pH or redox condition and then release it at a different pH or redox condition, and compositions and methods of preparation and use thereof.

7 Claims, 15 Drawing Sheets

(56) References Cited

PUBLICATIONS

Hydrogel: Preparation, characterization, and Application: A review (Journal of Advanced Research (2015) 6, 105-121) . (Year: 2015).*

* cited by examiner

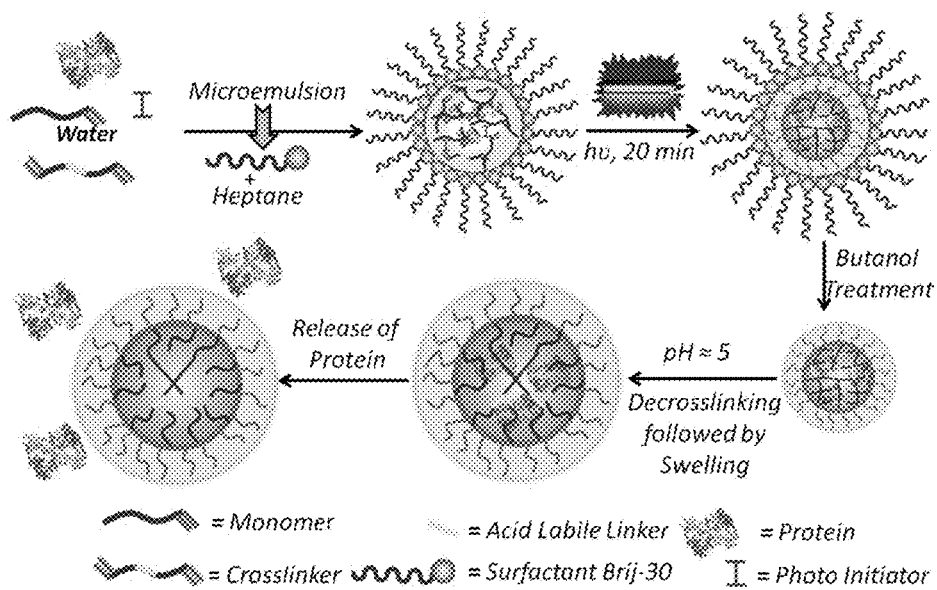
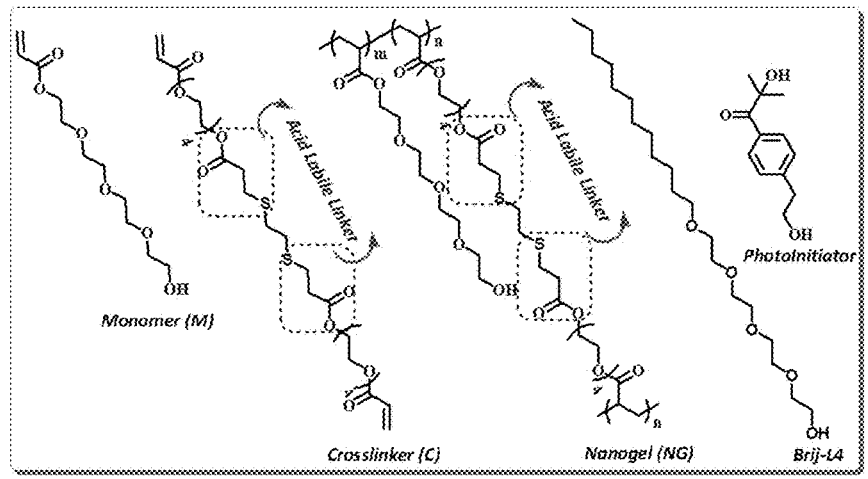
FIG. 1. *Scheme 1 Top*: Schematic presentation of protein encapsulation within the nanogel network and pH triggered release of the protein molecules. Protein structure on the above scheme is just a representative cartoon; *Bottom*: Molecular design of the surfactant, monomer, crosslinker, photoinitiator and nanogel.

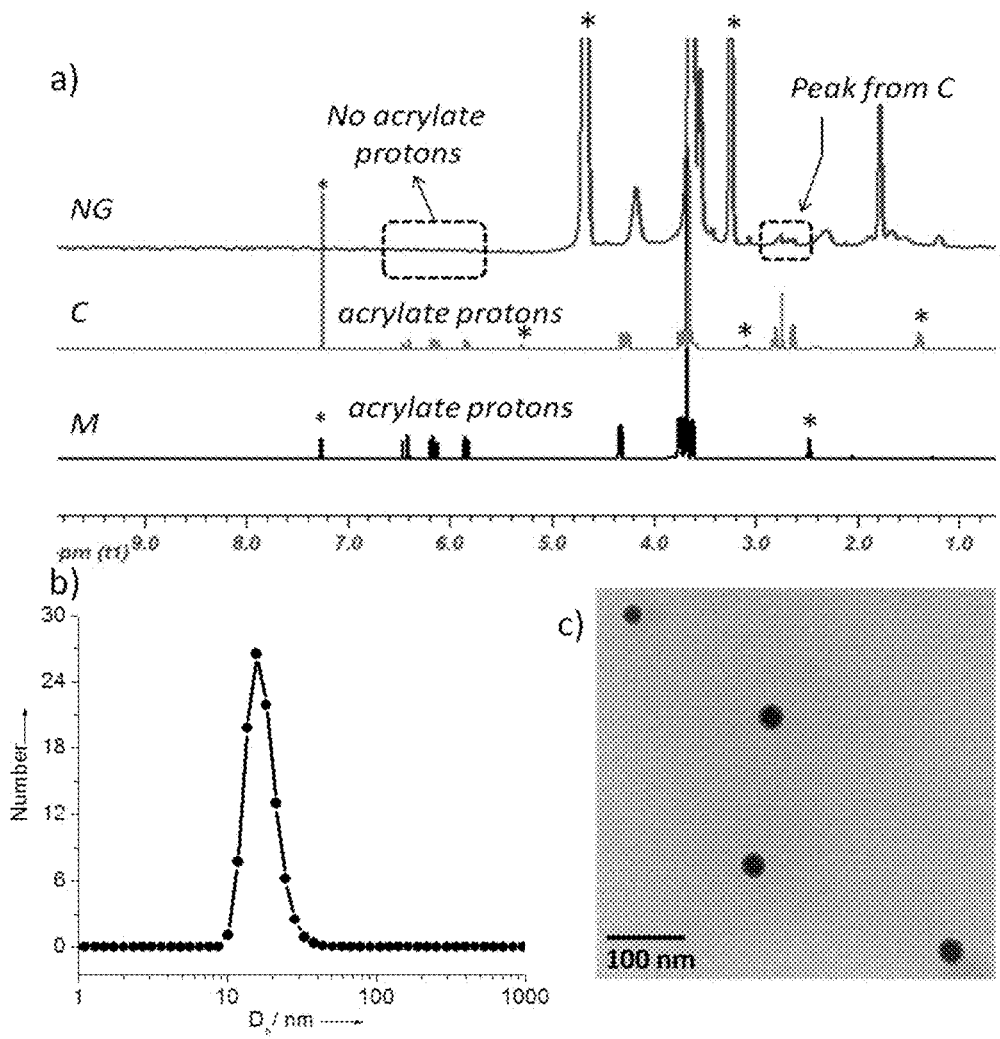
FIG. 2 (a) $^1$H-NMR spectra of monomer (M), crosslinker (C) and Nanogel without protein (NG). * indicates solvent peak and chemical shift values are shown in ppm on the X axis; (b) DLS spectrum of the NG; (c) HRTEM image of the NG (stained by 0.1 wt% uranyl acetate solution)

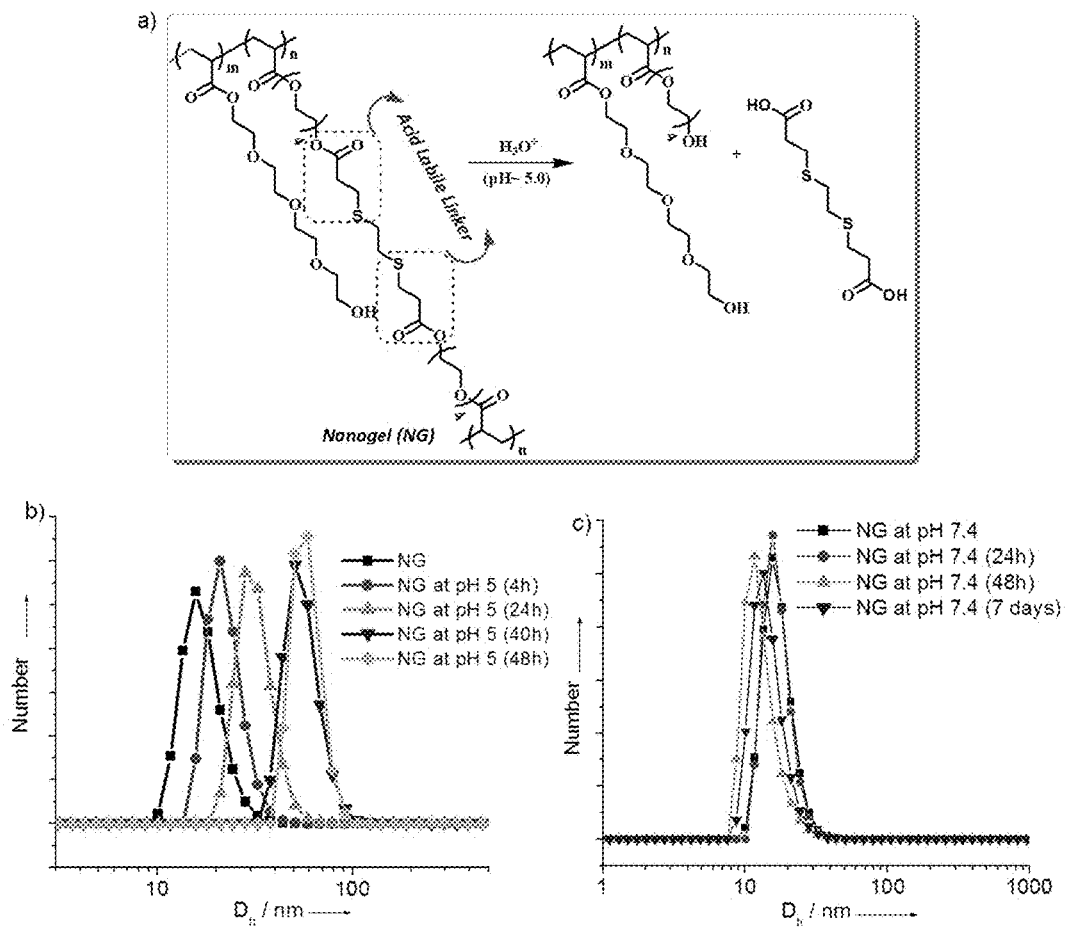
FIG. 3 (a) Acid induced hydrolysis of the β-thiopropionate functional group; (b) DLS profile of the nanogel at different time interval at pH 5.0; (c) DLS profile of the nanogel at different time interval at pH 7.4.

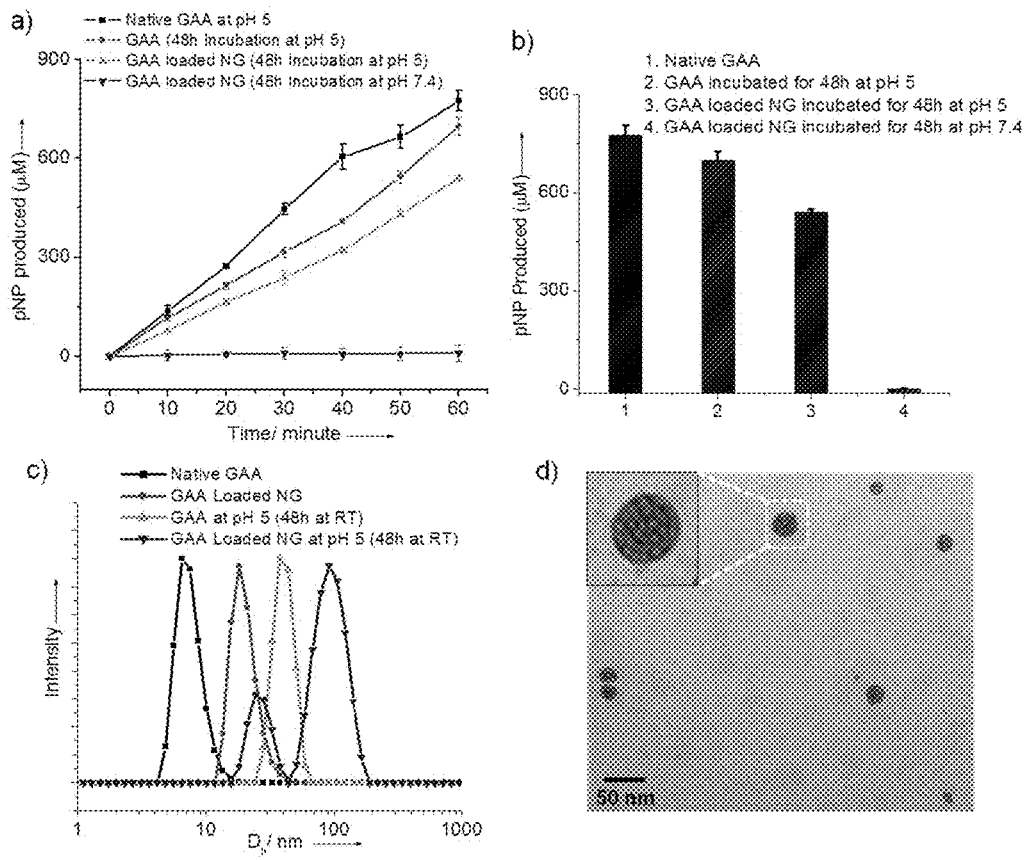

FIG. 4 (a) GAA activity assay after 48h incubation of the GAA loaded nanogel at pH 5.0 and pH 7.4: monitoring absorbance @ 400 nm of the pNP produced due to cleavage of the α -1, 4 linkages of para nitro phenol-α-D-glucopyranoside substrate;( b) Comparison of the endpoint activity; Protein concentration in each case = 0.173 µM; Temperature = 25°C; (c) Time variable DLS profile of native GAA and GAA loaded in the nanogel; (d) TEM image of GAA encapsulated NG; Inset: zoomed NG has shown.

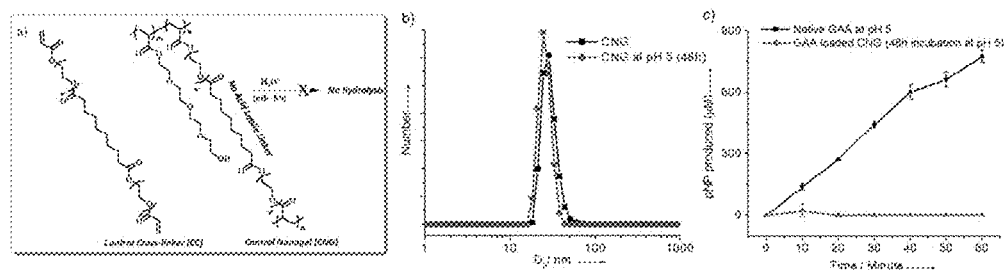
FIG. 5 (a) Structure of the control cross-linker and control nanogel (CNG); (b) DLS profile of the control nanogel after 48h incubation at pH 5.0; (c) GAA activity assay profile of control nanogel; Protein concentration = 0.173 μM. Temperature = 25°C.
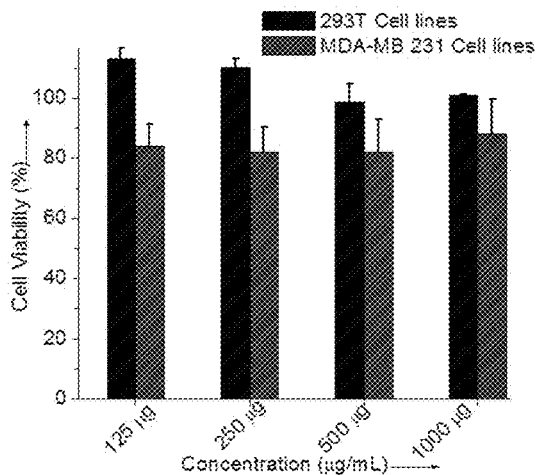
FIG. 6 *In vitro* cytoxicities of Nanogel (NG) on 293T cell (black) and MDA-MB 231 cell (red).

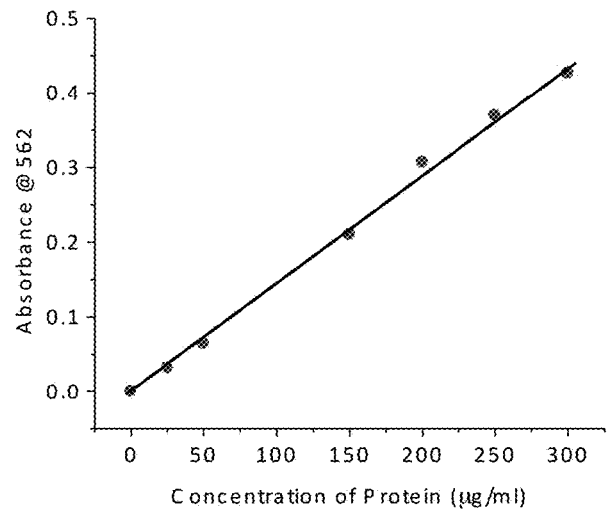
FIG. 7 Calibration curve using BCA assay; Absorbance monitored at 562 nm; Temperature = 25 °C.
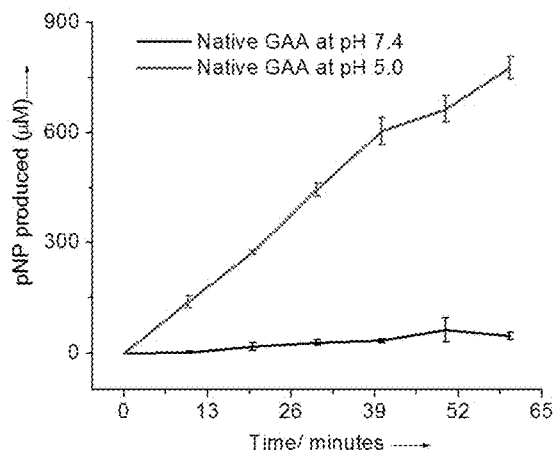
FIG. 8 Enzymatic activity of native GAA at pH 5.0 and pH 7.4; Temperature = 25 °C.

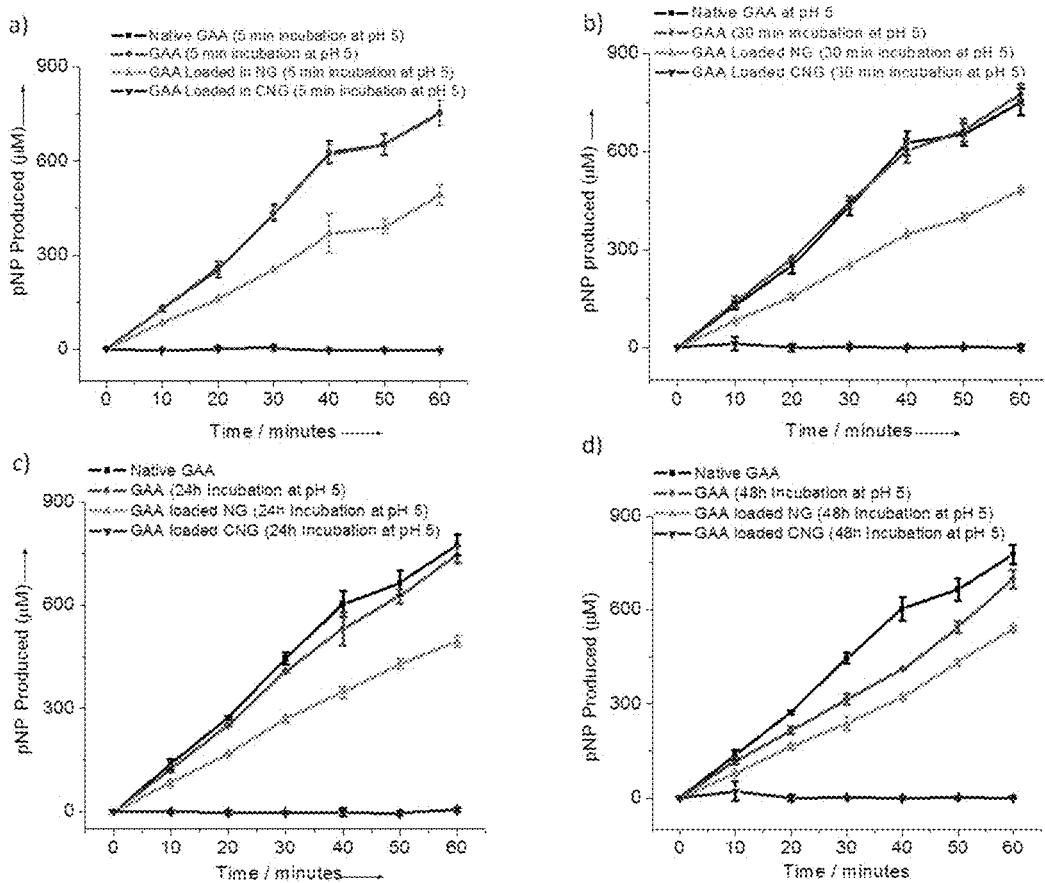
FIG. 9 Activity assay of the released GAA from the nanogel (NG) and control nanogel (CNG) at pH 5.0 and at different time interval; a) 5 min, b) 30 min, c) 24 h, and d) after 48 h incubation. Temperature = 25 °C.

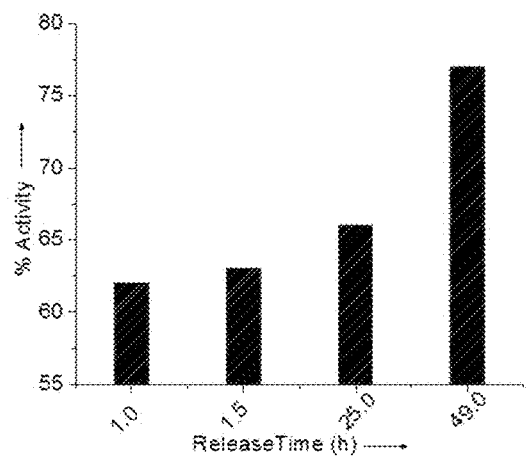
FIG. 10 % Activity of the released GAA from the nanogel over 49 h.
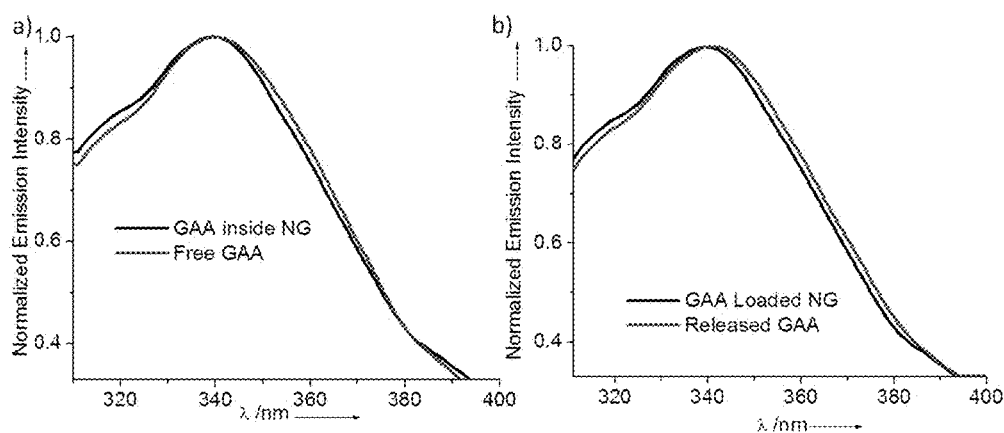
FIG. 11 a) Normalized emission spectra of the GAA loaded in the nanogel (black line) and native GAA (red line) at pH 7.4; b) Normalized emission spectra of GAA loaded in the nanogel (black line) and GAA released from nanogel after 48h incubation at pH 5.0 (red line); Tryptophan Excitation wavelength = 295 nm. Temperature = 25 °C.

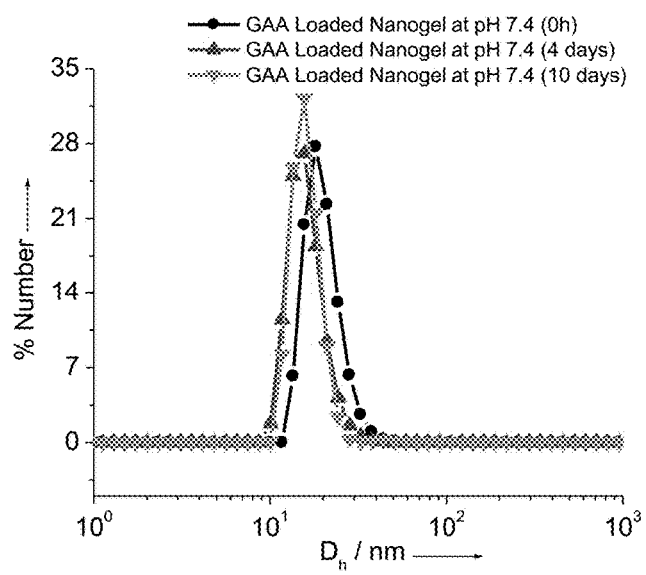
FIG. 12 DLS profile (PDI = 0.44, 0.40, 0.45) of the GAA loaded nanogel at pH 7.4. Even after 10 days there was no significant size change.
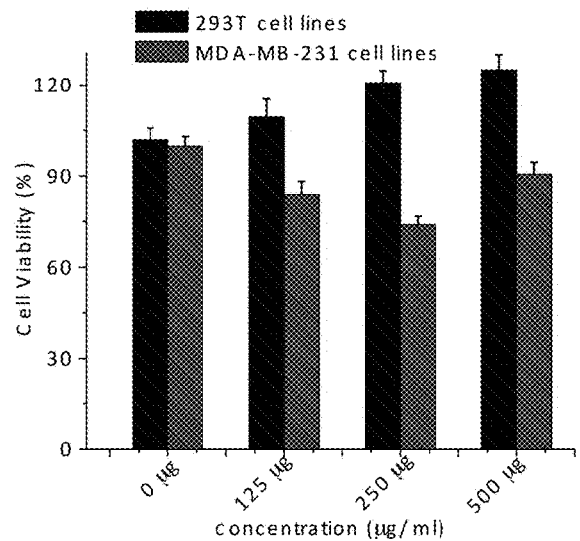
FIG. 13 *In vitro* cytoxicities of degraded nanogel on 293T cell (black) and MDA-MB 231 cell (red).

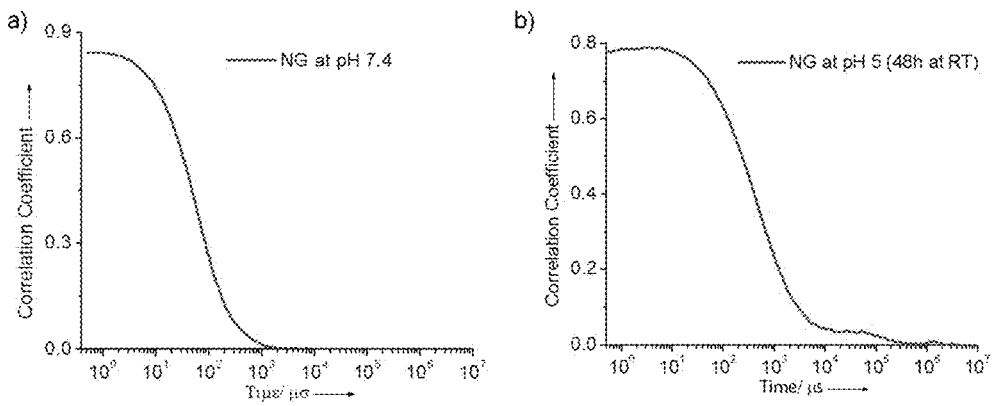

FIG. 14 Autocorrelation function for nanogel (NG) a) at pH 7.4 and b) at pH 5 (48 h incubation). For nanogel at pH 7.4 the smooth short decay time indicates one type of small size distribution. For swelled nanogel at pH 5.0 the slower decay indicates that larger aggregates are present in solution but also shows a slight bimodal distribution indicating the presence of other (larger) aggregates which can be correlated with DLS data and TEM data in Figure 3 in the main text.

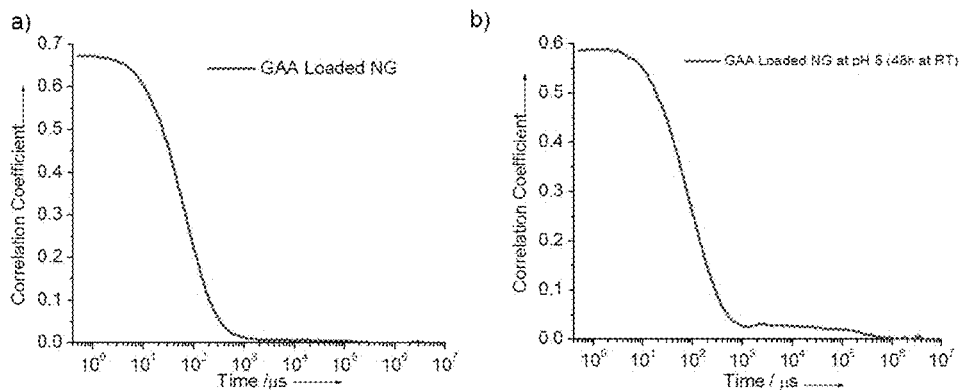

FIG. 15 Autocorrelation function for GAA loaded nanogel a) at pH 7.4 and b) at pH 5 (48 h incubation). For nanogel at pH 7.4 the smooth short decay time indicates one type of small size distribution. For swelled nanogel at pH 5.0 the slower decay indicates that larger aggregates are present in solution but also shows a slight bimodal distribution indicating the presence of other (larger) aggregates.

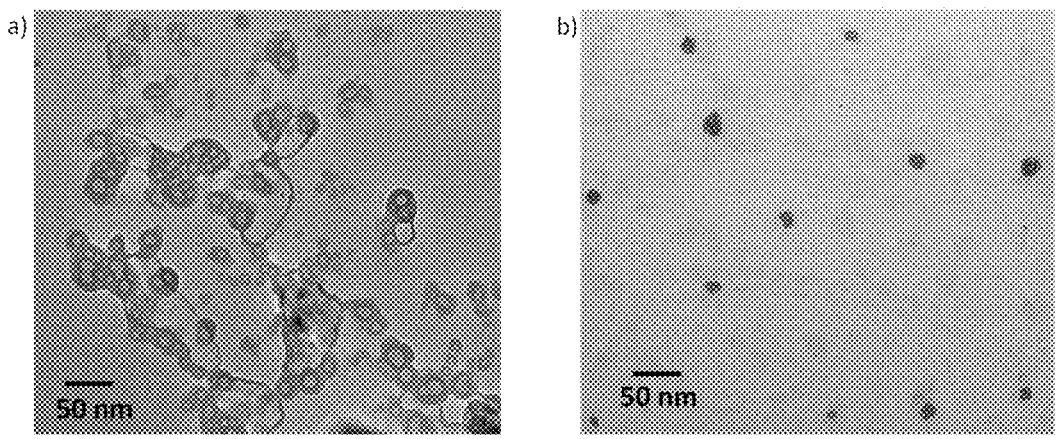
FIG. 16 Additional TEM images of a) Nanogel; b) GAA encapsulated nanogel.
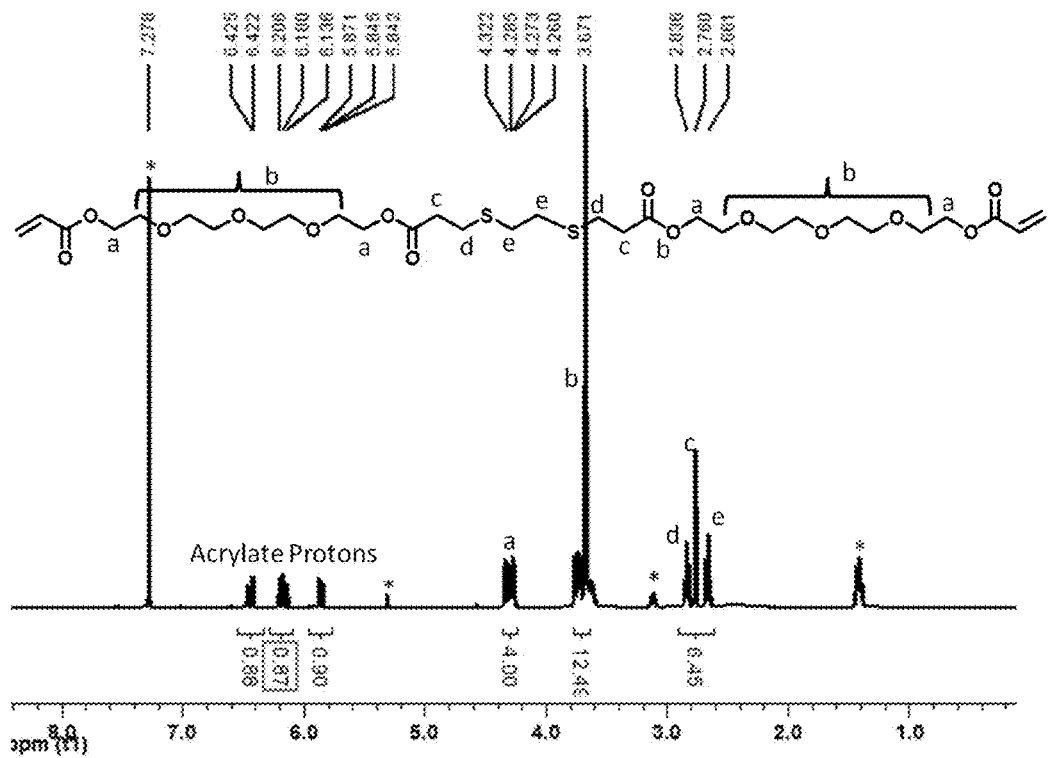
FIG. 17 NMR of Crosslinker (CC). * indicates solvent peak. The chemical shift values are shown on the X axis.

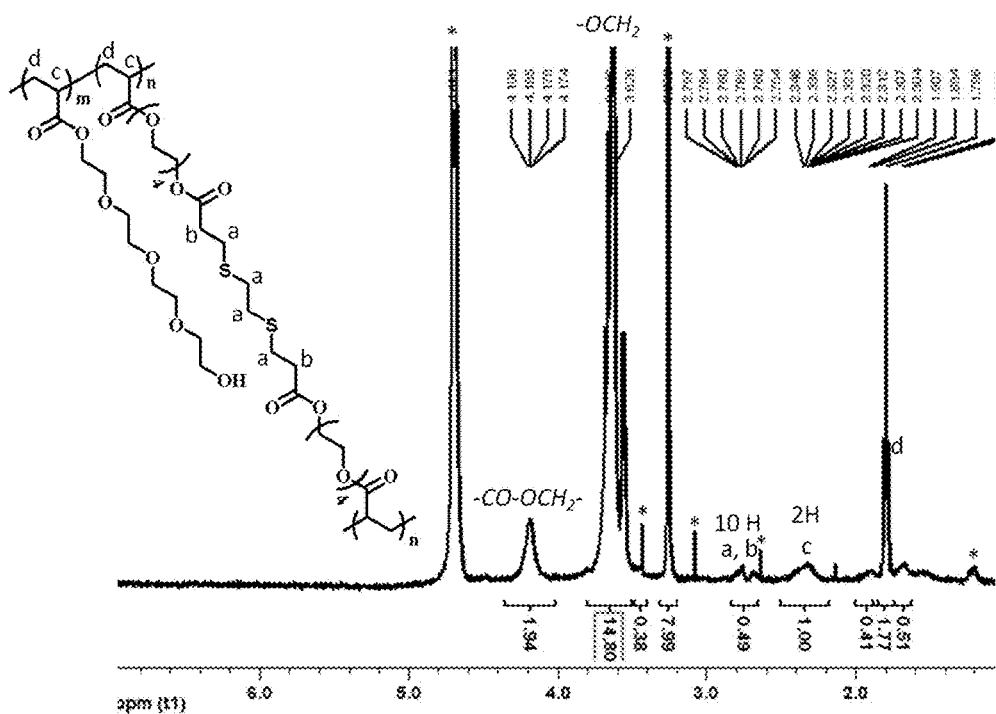
FIG. 18 NMR of Nanogel. * indicates solvent peak. The chemical shift values are shown on the X axis.
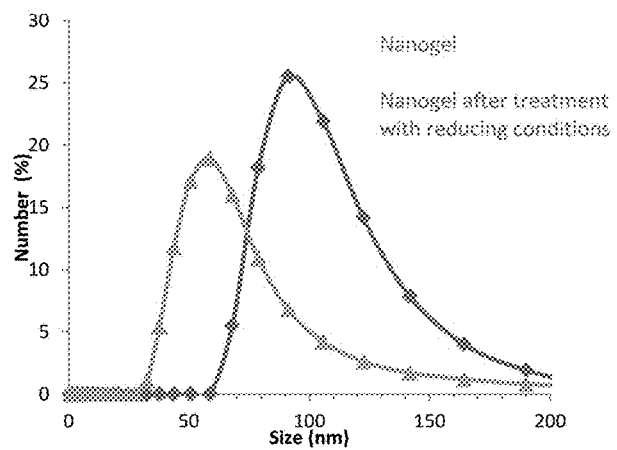
FIG. 19. Dynamic light scattering analysis to observe the size change of nanogels before and after treatment with reducing agent.

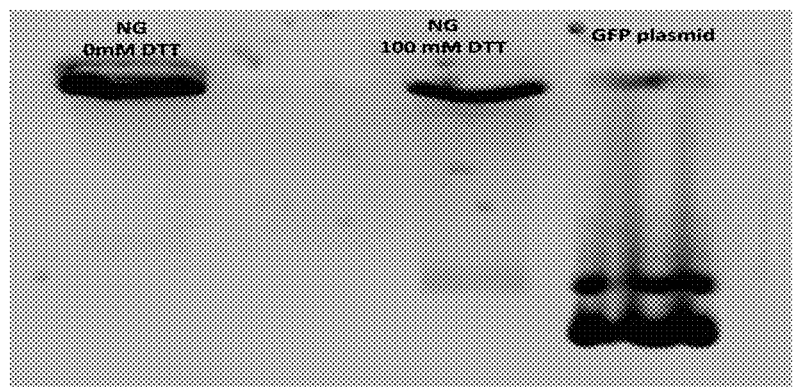

FIG. 20. Agarose gel electrophoresis assay to demonstrate the redox responsive behavior of plasmid encapsulated nanogels. Nanogels without reducing environment did not show a plasmid band and has intact nanogel with plasmid in the well. Nanogel treated with reducing environment shows a plasmid band and also reduced nanogel amount in the well.

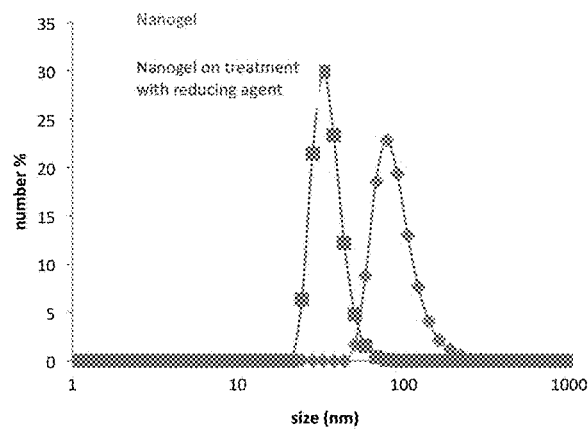

FIG. 21. Dynamic light scattering analysis to observe the size change of nanogels before and after treatment with reducing agent.

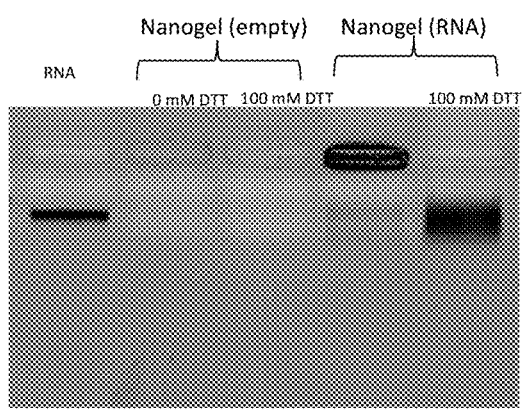

FIG. 22. Agarose gel electrophoresis assay to demonstrate the redox responsive behavior of ds RNA encapsulated nanogels. Nanogels without reducing environment did not show a RNA band and has intact nanogel with RNA in the well. Nanogel treated with reducing environment shows a RNA band and also reduced nanogel amount in the well.

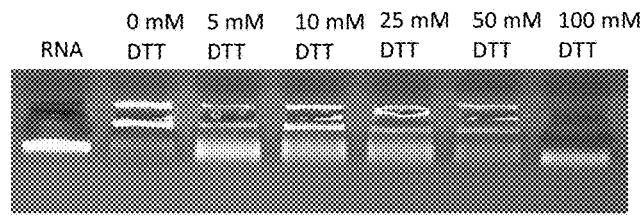

FIG. 23. Agarose gel electrophoresis assay to demonstrate the redox responsive behavior of ds RNA encapsulated nanogels upon responding to different concentrations of reducing agent

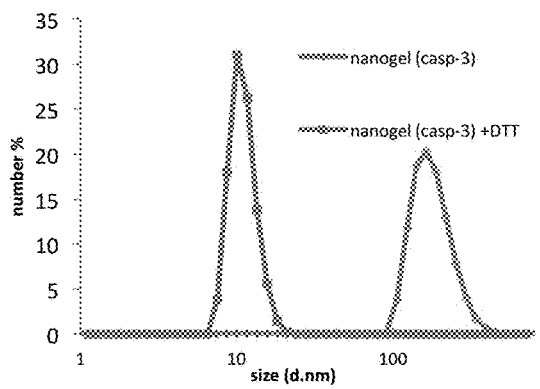

FIG. 24. Dynamic light scattering analysis to observe the size change of nanogels before and after treatment with reducing agent.

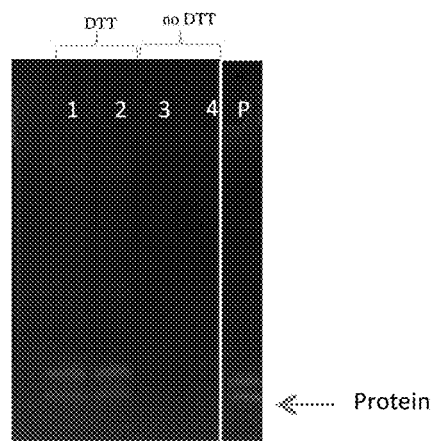

FIG. 25. SDS gel electrophoresis assay to demonstrate the redox responsive behavior of protein encapsulated nanogels. Nanogels without reducing environment did not show a protein band whereas nanogel treated with reducing environment shows a protein band.

POLYMERS AND POLYMERIC NANOGELS WITH HYDROPHILICS ENCAPSULATION AND RELEASE CAPABILITIES AND METHODS THEREOF

PRIORITY CLAIMS AND RELATED PATENT APPLICATIONS

This application is the U.S. national phase of and claims priority to PCT/US15/50810, filed Sep. 17, 2015, which claims the benefit of priority from U.S. Provisional Application Ser. No. 62/051,887, filed on Sep. 17, 2014, the entire content of each of which is incorporated herein by reference in its entirety.

STATEMENT OF FEDERALLY SPONSORED RESEARCH

This invention was made with U.S. Government support under Grant No. CHE-1307118 awarded by the National Science Foundation and GM-065255 awarded by the National Institutes of Health to the University of Massachusetts. The Government has certain rights in the invention.

TECHNICAL FIELDS OF THE INVENTION

The invention generally relates to polymers and polymer-based nano-structures. More particularly, the invention relates to charge-neutral, pH-responsive or redox-responsive polymeric nanogels that stably encapsulate an enzyme at one pH or redox condition then release it at a different pH or redox condition, and compositions and methods of preparation and use thereof, for example, in the treatment of lysosomal storage diseases.

BACKGROUND OF THE INVENTION

Recent years have seen increasing interests in molecular systems that enable stable encapsulation of a guest molecule in one environment and then controlled release of the guest molecule in a different environment. (Evans, et al. 1999 *The Colloidal Domain*, 2nd ed.; Wiley-VCH:New York; Holmberg, et al. 2003 *Surfactants and Polymers in Aqueous Solution*, 2nd ed.; John Wiley & Sons, Ltd: New York; Saito, et al. 2003 *Adv. Drug. Delivery Rev.* 55,199; Roy, et al. 2010 *Prog. Polym. Sci.* 35, 278; Guo, et al. 2014 *Acc. Chem. Res.*, 1925.) For example, various systems have been developed for hydrophobic small molecule guests using molecular cages and amphiphilic assemblies. (Liu, et al. 2000 *J. Controlled Release* 65,121; Gohy, et al. 2003 *Macromol. Chem. Phys.* 204, 1524; Zhong, et al. 2008 *Soft Matter* 4, 9; Bae, et al. 2009 *Adv. Drug Delivery Rev.* 61, 768; Kabanov, et al. 1995 *Macromolecules* 28, 2303; Allen, et al. 2004 *Science* 303, 1818; Formina, et al. 2010 *J. Am. Chem. Soc.* 132, 9540; Chacko, et al. 2012 *Adv. Drug Deliv. Rev.* 64, 836; Ryu, et al. 2010 *J. Am. Chem. Soc.* 132, 17227.)

In particular, there is a great need for developing encapsulation systems for proteins as the guest molecules, because imbalance in protein activity is the primary reason for most human pathology. (Gu, et al. 2011 *Chem. Soc. Rev.* 40, 3638; Walsh *Nat.* 2010 *Biotechnol.* 28, 917; Leader, et al. 2008 *Nat. rev. Drug Discov.* 7, 21.) When a protein is incorrectly overexpressed, common therapeutic approaches include small molecules that bind to the active site of the target and interference RNA molecules that slow down the protein expression. (Leader, et al. 2008 *Nat. rev. Drug Discov.* 7, 21; Desnick, et al. 2012 *Annu. Rev. Genomics Hum. Genet.* 13, 307; Parenti, et al. 2013 *Int. J. Mol. Med.* 31, 11.)

Developing a system for hydrophilic macromolecules, however, has been a significant challenge, since there is no contrast between the bulk and the host interior in water-soluble systems. (Mahmoud, et al. 2011 *Bioconjugate. Chem.* 22, 1416; Torchilin 2005 *Nat. Rev. Drug Discovery* 4, 145; Abu Lila, et al. 2009 *Expert Opin. Drug Delivery* 6, 1297; Eliaz, et al. 2004 *Cancer Res.* 64, 711; Haag, et al. 2006 *Angew. Chem. Int. Ed.* 2006, 45, 1198; *Angew. Chem.* 118, 1218; Murthy, et al. 2003 *Proc. Natl. Acad. Sci. U.S.A.* 100, 4995; Paramonov, et al. 2008 *Bioconjugate. Chem.* 19, 911; Kabanov, et al. 2009 *Angew. Chem. Int. Ed.*, 48, 5418; Kabanov, et al. 2009 *Angew. Chem.* 121, 5524.) Recently, supramolecular approaches in which an assembly responds to the presence of excess proteins are also being explored. (Savariar, et al. 2008 *J. Am. Chem. Soc.* 130, 5416; Takaoka, et al. 2009 *Nat. Chem.* 1, 557; Azagarsamy, et al. 2010 *J. Am. Chem. Soc.* 132, 4550; Mizusawa, et al. 2010 *J. Am. Chem. Soc.* 132, 729.) On the other hand, when the reduced activity of the protein causes a pathological condition, the options are relatively limited. Gene delivery approaches are promising, but the safety and efficacy of the delivery vehicles have limited their reach so far. (Mastrobattista, et al. 2006 *Nat. Rev. Drug Discovery* 5, 115; Pack, et al. 2005 *Nat. Rev. Drug Discovery* 4, 581; Ogris, et al. 1999 *Gene Ther.* 6, 595; Wattiaux, et al. 2000 *Adv Drug Delivery Rev.* 41, 201; Hunter *Adv.* 2006 *Drug Delivery Rev.* 58, 1523; Tang, et al. 1996 *Bioconjugate Chem.* 7, 703; Boussif, et al. 1995 *Proc. Natl. Acad. Sci. USA* 92, 7297.)

An alternative approach is to directly deliver the deficient proteins, which has the advantage of not causing artificial modifications in gene expression. (Gu, et al. 2011 *Chem. Soc. Rev.* 40, 3638.) Therefore, supramolecular assemblies that can robustly bind to protein molecules and release them in response to a stimulus are of great interest (Scheme 1, FIG. 1). Lysosomal storage diseases are caused by defective enzyme activity in any one of 50 lysosomal enzymes. The disorders, including Tay-Sachs, Fabry, Gaucher, and Pompe diseases, can be treated by delivery of recombinant enzyme to replace the missing enzymatic activity. Although enzyme replacement therapy is efficacious, it is also very inefficient, with less than 1% of the infused enzyme making it to the target tissues. (Desnick, et al. 2012 *Annu. Rev. Genomics Hum. Genet.* 13, 307.)

Nanoparticles have played an increasingly significant role in diverse fields such as microelectronics, multiphase catalysis, sensing and therapeutics. There have been several nanoscopic systems involving polymeric molecules and proteins, as applicable to protein delivery. (Gu, et al. 2011 *Chem. Soc. Rev.* 40, 3638.) A commonly reported approach involves covalent conjugation of proteins to polymers using the side chain functional groups or using the initiating/terminating functional group at the chain terminus. (González-Toro, et al. 2013 *Eur. Poly. J.* 49, 2906.) Non-covalent binding between proteins and polymers have also been approached. Most of these systems use charge complementarity between a polyelectrolyte and the surface charge of the protein as the basis for the formation of the nanoparticle. While this electrostatics-based approach has the advantage of being simple, sterics-based encapsulation has the advantage of providing charge-neutral systems that are often desired for avoiding non-specific interactions based complexities.

Thus, an urgent unmet need remains in developing polymeric nanogels that encapsulate a guest biomolecule stably in one environment and then release it in a different environment in controlled fashion.

SUMMARY OF THE INVENTION

The invention provides novel polymeric nanogels that have charge-neutral surface functionalities and are pH- or redox-responsive and can stably encapsulate a hydrophilic biomolecule at one pH or redox condition and then release it at a different pH or redox condition, and compositions and methods of preparation and use thereof. As a delivery vehicle, for example, a biomolecular cargo (e.g., enzyme or nucleic acid) is encapsulated via crosslinking with a cross-linker having a stimulus-sensitive functionality (e.g., β-thio-esters) and is transported to but releasable at the desired location with a proper stimuli, a change in pH change or conditions.

This approach of reversible protein encapsulation and release can be utilized in a broad range of biological applications. Various diseases and disorders may be treated according to this strategy by delivering relevant enzymes or nucleic acids to a particular disease site. An example of such a disease is of lysosomal storage diseases.

In one aspect, the invention generally relates to a cross-linked polymeric nanogel, adapted to stably encapsulate a biomolecule at a first pH or redox condition and then release it at a second pH or redox condition, respectively.

In another aspect, the invention generally relates to a nano-assembly. The nano-assembly includes: a host cross-linked polymer network; and a guest biomolecule cargo non-covalently encapsulated in the host crosslinked polymer network. The host crosslinked polymer network is stable at a first pH or redox condition and is adapted to be addressable by a change of environmental pH or redox condition to a second pH or redox condition, which results in partial or complete descrosslinking of the host polymer network and release of the guest biomolecule cargo from the nano-assembly.

In yet another aspect, the invention generally relates to a method for controlled delivery of a biomolecule to a target biological site. The method includes: providing a nano-assembly of a host crosslinked polymer network non-covalently encapsulating therein a guest biomolecule at a first pH or a redox condition, wherein the host crosslinked polymer network is adapted to to be addressable by a change of environmental pH or redox condition to a second pH resulting in release of the guest biomolcular cargo from the nano-assembly; delivering the nano-assembly to the target biological site; and causing a change of environmental pH or redox condition to a second pH or redox condition resulting in a partial or complete decrosslinking resulting in release of the guest biomolecule from the nano-assembly.

BRIEF DESCRIPTION OF THE DRAWINGS

FIG. 1. Scheme 1 Top: Schematic presentation of protein encapsulation within the nanogel network and pH triggered release of the protein molecules. Protein structure on the above scheme is just a representative cartoon; Bottom: Molecular design of the surfactant, monomer, crosslinker, photoinitiator and nanogel.

FIG. 2 (a) $^1$H-NMR spectra of monomer (M), crosslinker (C) and Nanogel without protein (NG). * indicates solvent peak and chemical shift values are shown in ppm on the X axis; (b) DLS spectrum of the NG; (c) HRTEM image of the NG (stained by 0.1 wt % uranyl acetate solution)

FIG. 3 (a) Acid induced hydrolysis of the β-thiopropionate functional group; (b) DLS profile of the nanogel at different time interval at pH 5.0; (c) DLS profile of the nanogel at different time interval at pH 7.4.

FIG. 4 (a) GAA activity assay after 48 h incubation of the GAA loaded nanogel at pH 5.0 and pH 7.4: monitoring absorbance @t 400 nm of the pNP produced due to cleavage of the α-1, 4 linkages of para nitro phenol-α-D-glucopyranoside substrate; (b) Comparison of the endpoint activity; Protein concentration in each case=0.173 μM; Temperature=25° C.; (c) Time variable DLS profile of native GAA and GAA loaded in the nanogel; (d) TEM image of GAA encapsulated NG; Inset: zoomed NG has shown.

FIG. 5 (a) Structure of the control cross-linker and control nanogel (CNG); (b) DLS profile of the control nanogel after 48 h incubation at pH 5.0; (c) GAA activity assay profile of control nanogel; Protein concentration=0.173 μM. Temperature=25° C.

FIG. 6 In vitro cytoxicities of Nanogel (NG) on 293T cell (black) and MDA-MB 231 cell (red).

FIG. 7: Calibration curve using BCA assay; Absorbance monitored at 562 nm; Temperature=25° C.

FIG. 8: Enzymatic activity of native GAA at pH 5.0 and pH 7.4; Temperature=25° C.

FIG. 9: Activity assay of the released GAA from the nanogel (NG) and control nanogel (CNG) at pH 5.0 and at different time interval; a) 5 min, b) 30 min, c) 24 h, and d) after 48 h incubation. Temperature=25° C.

FIG. 10: % Activity of the released GAA from the nanogel over 49 h.

FIG. 11: a) Normalized emission spectra of the GAA loaded in the nanogel (black line) and native GAA (red line) at pH 7.4; b) Normalized emission spectra of GAA loaded in the nanogel (black line) and GAA released from nanogel after 48 h incubation at pH 5.0 (red line); Tryptophan Excitation wavelength=295 nm. Temperature=25° C.

FIG. 12: DLS profile (PDI=0.44, 0.40, 0.45) of the GAA loaded nanogel at pH 7.4. Even after 10 days there was no significant size change.

FIG. 13: In vitro cytoxicities of degraded nanogel on 293T cell (black) and MDA-MB 231 cell (red).

FIG. 14: Autocorrelation function for nanogel (NG) a) at pH 7.4 and b) at pH 5 (48 h incubation). For nanogel at pH 7.4 the smooth short decay time indicates one type of small size distribution. For swelled nanogel at pH 5.0 the slower decay indicates that larger aggregates are present in solution but also shows a slight bimodal distribution indicating the presence of other (larger) aggregates which can be correlated with DLS data and TEM data in FIG. 3 in the main text.

FIG. 15: Autocorrelation function for GAA loaded nanogel a) at pH 7.4 and b) at pH 5 (48 h incubation). For nanogel at pH 7.4 the smooth short decay time indicates one type of small size distribution. For swelled nanogel at pH 5.0 the slower decay indicates that larger aggregates are present in solution but also shows a slight bimodal distribution indicating the presence of other (larger) aggregates.

FIG. 16: Additional TEM images of a) Nanogel; b) GAA encapsulated nanogel.

FIG. 17: NMR of Crosslinker (CC). * indicates solvent peak. The chemical shift values are shown on the X axis.

FIG. 18: NMR of Nanogel. * indicates solvent peak. The chemical shift values are shown on the X axis.

FIG. 19. Dynamic light scattering analysis to observe the size change of nanogels before and after treatment with reducing agent.

FIG. 20. Agarose gel electrophoresis assay to demonstrate the redox responsive behavior of plasmid encapsulated nanogels. Nanogels without reducing environment did not show a plasmid band and has intact nanogel with plasmid in the well. Nanogel treated with reducing environment shows a plasmid band and also reduced nanogel amount in the well.

FIG. 21. Dynamic light scattering analysis to observe the size change of nanogels before and after treatment with reducing agent.

FIG. 22. Agarose gel electrophoresis assay to demonstrate the redox responsive behavior of ds RNA encapsulated nanogels. Nanogels without reducing environment did not show a RNA band and has intact nanogel with RNA in the well. Nanogel treated with reducing environment shows a RNA band and also reduced nanogel amount in the well.

FIG. 23. Agarose gel electrophoresis assay to demonstrate the redox responsive behavior of ds RNA encapsulated nanogels upon responding to different concentrations of reducing agent.

FIG. 24. Dynamic light scattering analysis to observe the size change of nanogels before and after treatment with reducing agent.

FIG. 25. SDS gel electrophoresis assay to demonstrate the redox responsive behavior of protein encapsulated nanogels. Nanogels without reducing environment did not show a protein band whereas nanogel treated with reducing environment shows a protein band.

DEFINITIONS

Definitions of specific functional groups and chemical terms are described in more detail below. General principles of organic chemistry, as well as specific functional moieties and reactivity, are described in "Organic Chemistry", Thomas Sorrell, University Science Books, Sausalito: 2006. It will be appreciated that the compounds, as described herein, may be substituted with any number of substituents or functional moieties.

As used herein, "$C_x$-$C_y$" refers in general to groups that have from x to y (inclusive) carbon atoms. Therefore, for example, $C_1$-$C_6$ refers to groups that have 1, 2, 3, 4, 5, or 6 carbon atoms, which encompass $C_1$-$C_2$, $C_1$-$C_3$, $C_1$-$C_4$, $C_1$-$C_5$, $C_2$-$C_3$, $C_2$-$C_4$, $C_2$-$C_5$, $C_2$-$C_6$, and all like combinations. "$C_1$-$C_{15}$", "$C_1$-$C_{20}$" and the likes similarly encompass the various combinations between 1 and 20 (inclusive) carbon atoms, such as $C_1$-$C_6$, $C_1$-$C_{12}$, $C_3$-$C_{12}$ and $C_6$-$C_{12}$.

As used herein, the term "alkyl", refers to a hydrocarbyl group, which is a saturated hydrocarbon radical having the number of carbon atoms designated and includes straight, branched chain, cyclic and polycyclic groups. The term "hydrocarbyl" refers to any moiety comprising only hydrogen and carbon atoms. Hydrocarbyl groups include saturated (e.g., alkyl groups), unsaturated groups (e.g., alkenes and alkynes), aromatic groups (e.g., phenyl and naphthyl) and mixtures thereof.

As used herein, the term "$C_x$-$C_y$" alkyl refers to a saturated linear or branched free radical consisting essentially of x to y carbon atoms, wherein x is an integer from 1 to about 10 and y is an integer from about 2 to about 20. Exemplary $C_x$-$C_y$ alkyl groups include "$C_1$-$C_{20}$ alkyl," which refers to a saturated linear or branched free radical consisting essentially of 1 to 20 carbon atoms and a corresponding number of hydrogen atoms. Exemplary $C_1$-$C_{20}$ alkyl groups include methyl, ethyl, n-propyl, isopropyl, n-butyl, isobutyl, dodecanyl, etc.

As used herein, the term "halogen" refers to fluorine (F), chlorine (Cl), bromine (Br), or iodine (I).

DESCRIPTION OF THE INVENTION

The invention provides novel polymeric nanogels that are charge-neutral and pH- or redox-responsive and can stably encapsulate a hydrophilic biomolecule at one set of pH or redox conditions and then release it at another set of different pH or redox conditions, and compositions and methods of preparation and use thereof. For example, in the case of pH-responsive release, β-thioesters can be used as the stimulus-sensitive functionality where the enzyme encapsulation by nanogel crosslinking is stable at a neutral pH, but releasable at low pH. The nanomaterials platform of reversible protein encapsulation and release can be utilized in a rather broad range of biological applications. Various diseases and disorders may be treated according to this strategy by delivering relevant enzymes to particular disease site. An example of such a disease is of lysosomal storage diseases.

The polymers, polymeric nanogels and protein delivery vehicles of the invention can be prepared via simple and reliable synthetic techniques.

In one aspect, the invention generally relates to a crosslinked polymeric nanogel, adapted to stably encapsulate a hydrophilic biomolecule at a first pH or redox condition and then release it at a second pH or redox condition, respectively.

In certain preferred embodiments, the crosslinked polymeric nanogel is a pH-responsive polymeric nanogel adapted to stably encapsulate a biomolecule at a first pH and then release it at a second pH.

In certain preferred embodiments, the crosslinked polymeric nanogel is a redox-responsive polymeric nanogel adapted to stably encapsulate a biomolecule at a first redox condition and then release it at a second redox condition.

In certain embodiments, the biomolecule is selected from polypeptides, carbohydrates or nucleic acids. In certain preferred embodiments, the polypeptide is a protein, enzyme, antibody, antibody fragment, polypeptide aptamer, or a small polypeptide fragment. In certain preferred embodiments, the nucleic acid is an oligonucleotide, nucleic acid aptamer, a single-strand or double strand DNA or RNA.

In certain preferred embodiments, the surface functionalities of the crosslinked polymeric nanogel is charge-neutral.

In certain preferred embodiments, the crosslinked polymeric nanogel is crosslinked with an acid-labile crosslinker. Any suitable acid-labile crosslinker may be utilized. In certain embodiments, the acid-labile crosslinker comprises one or more moieties selected from β-thiopropionate, β-thiopropionate thioester, carbamate, hydrazone and imine moieties. In certain preferred embodiments, the acid-labile crosslinker comprises a β-thiopropionate moiety.

In certain preferred embodiments, the crosslinked polymeric nanogel comprises a structural unit of:

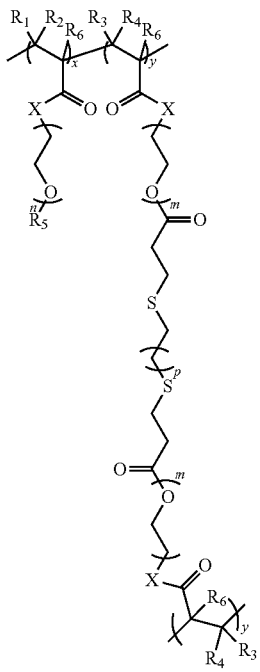

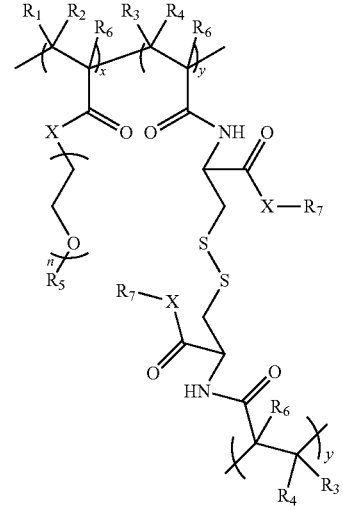

wherein each of $R_1$, $R_2$, $R_3$ $R_4$, $R_5$ and $R_6$ is independently a hydrogen, $C_1$-$C_{12}$ alkyl group, or halogen;

each of x and y is independently a positive number;

each of m and p is independently an integer from about 1 to about 10 (e.g., 1, 2, 3, 4, 5, 6, 7, 8, 9, 10).

n is a positive number from 1 to about 200 (e.g., from 1 to about 50, from 1 to about 100, from 1 to about 150); and X is independently chosen from O and NH.

In certain preferred embodiments, each of $R_1$, $R_2$, $R_3$ $R_4$, $R_5$ and $R_6$ is a hydrogen.

In certain preferred embodiments, the second pH is lower than the first pH. In certain embodiments, the second pH is from about 3.5 to about 6.4 and the first pH is from about 6.5 to about 8.0. In certain preferred embodiments, the second pH is from about 4.8 to about 5.3 (e.g., 4.8, 4.9, 5.0, 5.1, 5.2, 5.3) and the first pH is from about 6.8 to about 7.4 (e.g., 6.8, 6.9, 7.0, 7.1, 7.2, 7.3).

In certain preferred embodiments, the crosslinked polymeric nanogel is crosslinked with a redox-labile crosslinker. Any suitable redox-labile crosslinker may be utilized. In certain embodiments, the redox-labile crosslinker comprises one or more moieties selected from acrylate, methacrylate, disulfide functionalities.

In certain preferred embodiments, the crosslinked polymeric nanogel comprises a structural unit:

wherein each of $R_1$, $R_2$, $R_3$ $R_4$, $R_5$ and $R_6$ is independently a hydrogen, $C_1$-$C_{12}$ alkyl group, or halogen;

$R_7$ is independently a hydrogen, $C_1$-$C_{12}$ alkyl group, or an ethyleneglycol chain with 2 to about 200 (e.g., 2 to about 50; 2 to about 100, 2 to about 150) repeat units;

each of x and y is independently a positive number;

n is a positive number from 1 to about 200 (e.g., from 1 to about 50, from 1 to about 100, from 1 to about 150); and X is independently chosen from O or NH.

In certain preferred embodiments, each of $R_1$, $R_2$, $R_3$ $R_4$, $R_5$ and $R_6$ is a hydrogen.

In another aspect, the invention generally relates to a nano-assembly. The nano-assembly includes: a host crosslinked polymer network; and a guest biomolecule cargo non-covalently encapsulated in the host crosslinked polymer network. The host crosslinked polymer network is stable at a first pH or redox condition and is adapted to be addressable by a change of environmental pH or redox condition to a second pH or redox condition, which results in partial or complete descrosslinking of the host polymer network and release of the guest biomolecule cargo from the nano-assembly. In certain preferred embodiments, the guest biomolecule is hydrophilic.

In certain embodiments, the acid-labile crosslinker comprises one or more moieties selected from β-thiopropionate, β-thiopropionate thioester, carbamate, hydrazone and imine moieties. In certain embodiments, the acid-labile crosslinker comprises a β-thiopropionate moiety. In certain preferred embodiments of the nano-assembly, the host crosslinked polymer network is a pH-responsive polymeric nanogel adapted to stably encapsulate a biomolecule at a first pH and then release it at a second pH. In certain embodiments of the nano-assembly, the second pH is lower than the first pH. In certain embodiments, the second pH is from about 3.5 to about 6.4 and the first pH is from about 6.5 to about 8.0. In certain preferred embodiments, the second pH is from about 4.8 to about 5.3 (e.g., 4.8, 4.9, 5.0, 5.1, 5.2, 5.3) and the first pH is from about 6.8 to about 7.4 (e.g., 6.8, 6.9, 7.0, 7.1, 7.2, 7.3).

In certain preferred embodiments of the nano-assembly, the host crosslinked polymer network is a redox-responsive polymeric nanogel adapted to stably encapsulate a biomolecule at a first redox condition and then release it at a second redox condition.

In certain embodiments of the nano-assembly, the biomolecule is selected from polypeptides, carbohydrates, nucleic acids or peptide nucleic acids. In certain embodiments, the polypeptide is a protein, enzyme, antibody, antibody fragment, polypeptide aptamer, or a small polypeptide fragment. In certain embodiments, the nucleic acid is an oligonucleotide, nucleic acid aptamer, a single-strand or double strand DNA or RNA.

In certain embodiments of the nano-assembly, the polypeptide is an enzyme selected from acid α-glucosidase (GAA), N-acetylglucosamine-1-phosaphate transferase, Cathepsin A, sulfatases, Niemann-Pick C1 and C2, sphingolipid activator proteins, sialin, or other enzymatic and non-enzymatic proteins involved lysosomal storage diseases.

In certain embodiments of the nano-assembly, the cross-linked polymeric nanogel is charge-neutral.

In yet another aspect, the invention generally relates to a method for controlled delivery of a biomolecule to a target biological site. The method includes: providing a nano-assembly of a host crosslinked polymer network non-covalently encapsulating therein a guest biomolecule at a first pH or a redox condition, wherein the host crosslinked polymer network is adapted to to be addressable by a change of environmental pH or redox condition to a second pH resulting in release of the guest protein cargo from the nano-assembly; delivering the nano-assembly to the target biological site; and causing a change of environmental pH or redox condition to a second pH or redox condition resulting in a partial or complete decrosslinking resulting in release of the guest biomolecule from the nano-assembly. In certain preferred embodiments, the guest biomolecule is hydrophilic.

Any suitable biomolecular cargo may be used, for example, polypeptides, carbohydrates, nucleic acids or peptide nucleic acids. For example, the polypeptide may be selected from a protein, enzyme, antibody, antibody fragment, polypeptide aptamer, or a small polypeptide fragment and the nucleic acid may be selected from an oligonucleotide, nucleic acid aptamer, a single-strand or double strand DNA or RNA. For example, the polypeptide may be an enzyme selected from acid α-glucosidase (GAA), N-acetylglucosamine-1-phosaphate transferase, Cathepsin A, sulfatases, Niemann-Pick C1 and C2, sphingolipid activator proteins, sialin, or other enzymatic and non-enzymatic proteins involved lysosomal storage diseases. Preferably, the encapsulated biomolecule is inactive and recovers at least 50% (preferably at least 60%, 70%, 80%, or 90%) of ist activity upon its release from encapsulation at the second pH or redox condition.

An important feature of the cross-linked polymeric nanogels of the invention is that these scaffolds have the advantage of being concentration-independent; i.e. once formed the assembly is stable even at very high dilutions, as they do not require a critical aggregation concentration that are typical for amphiphilic assemblies such as micelles and vesicles.

Acid α-glucosidase (GAA) is selected as the guest enzyme in certain embodiments of the invention because GAA is a lysosomal enzyme and is enzymatically active at lysozymal pH (pH≈5), but inactive at neutral pH. This enzymatic guest provides a useful read-out for the stimulus-sensitive supramolecular chemistry targeted in this work. Defective GAA is responsible for the lysosomal storage disorder known as Pompe disease, which highlights the disease-relevance of this combination. Additionally, β-thioester is selected as the pH-sensitive crosslinking functional group for some embodiments because: (i) it is stable at neutral pH and is hydrolyzable at lower pH (<pH≈5.3); (ii) the half-life of the functional group is relatively long and therefore provides an opportunity for a sustained release of the cargo. (Oishi, et al. 2003 *Biomacromolecules* 4, 1426-1432; Oishi, et al. 2005 *J. Am. Chem. Soc.* 127, 1624; Dan, et al. 2011 *Langmuir* 27, 612; Dan, et al. 2013 *Angew Chemie*. 125, 7441; Dan, et al. 2013 *Angew. Chem. Int. Ed.* 52, 7300; Schoenmakers, et al. 2004 *J. Control. Release* 95, 291.)

Shown in Scheme 1 (FIG. 1) are exemplary structures of the monomers and cross-linker according to the invention. In certain embodiments, the monomer is based on a charge neutral tetra-oligoethyleneglycol, as these monomers typically render the systems biocompatible and obviate the electrostatic-based non-specific interactions between the enzymatic guest $^{and}$ the host assembly. The β-thioester based cross-linker also contains oligothyleneglycol units to endow them with the water solubility needed for convenient incorporation of the crosslinking monomer in the aqueous phase during the nanogel synthesis using inverse emulsion polymerization. (Schillemans, et al. 2006 *Macromolecules* 39, 5885; Lawrence, et al. 2000 *Adv. Drug Deliv. Rev.* 45, 89; Azagarsamy, et al. 2012 *Biomacromolecules* 13, 2219.) The water-soluble monomers and crosslinkers, combined with the nanogel synthesis in a w/o emulsion polymerization, also provides an opportunity for the in situ encapsulation of the water-soluble enzymatic guest in a water-soluble nanocontainer.

As disclosed herein, the inverse emulsion was formed using heptane as the continuous phase and Brij L4 as the surfactant. The polymerization between the monomer and the cross-linker was initiated within the dispersed aqueous phase of the w/o emulsion using 2-hydroxy-4'-(2-hydroxyethoxy)-2-methylpropiophenone as the photoinitiator. The reaction vessel containing the reaction mixture was exposed to UV light with mild stirring for 20 minutes. After the polymerization, the surfactants were removed by addition of n-butanol and PBS buffer, followed by centrifugation. The resultant aqueous solution was dialyzed against PBS buffer for 24 h at 5° C. to obtain the protein-encapsulated nanogel.

The nanogels were characterized by $^1$H-NMR spectroscopy (FIG. 2a). First, there were no signals from the acrylate protons in the $^1$H-NMR spectrum of the NG, indicating complete conversion of the acrylate monomer. Second, the polymer contains both the TEG-acrylate monomer and the β-thioester cross-linker incorporated into the nanogel. Note that the signal at 2.6-2.8 ppm corresponds to the β-protons of the β-thioester. From the integration, the percentage of cross-linker was found to correspond to the feed-ratio of the monomers at ~5%. The nanogels that are buried within the interiors of the nanogel are discernible in the NMR, also supporting the low crosslink density of 5%. To examine the size of the nanogel particle dynamic light scattering (DLS) experiments were carried out, which indicated an average hydrodynamic diameter ($D_h$) of about 16 nm for the nanogels (FIG. 2b). The 10-20 nm sizes data using transmission electron microscopy (TEM) (FIG. 2c) was in agreement with the DLS results.

To investigate the decrosslinking phenomenon in the nanogel due to hydrolytic cleavage of the β-thiopropionate linker in acidic conditions, (FIG. 3a) the nanogel solution was treated with acetate buffer, where the pH of the solution was maintained at 5.0. The variations in the nanogel were monitored by assessing size change using DLS over time (FIG. 3b). The average size of the nanogel increased over time (from ~18 nm to ~60 nm) at pH 5.0, which is attributed to decrosslinking-induced swelling. The larger size particle formation is attributed to acid induced swelling which eventually leads to interparticle fusion. The observed size increase due to decrosslinking-induced swelling has precedence in literature.[47]

To further verify the size change, analysis of the dried sample of decrosslinked nanogel (aliquot taken after 48 h) using TEM revealed presence of spherical particle in the range of 40 nm to 70 nm, along with a few even larger particles (more than 100 nm in size). The larger particles that are likely to occur due to interparticle fusion are observed in DLS also, when investigated using volume-based assessment of the scattering data. Overall, the TEM data corroborates very well with the DLS data. To confirm whether decosslinking induced swelling occurs selectively in acidic pH, time variable DLS (FIG. 3c) of the nanogel at pH 7.4 was monitored. Even after 7 days there was no change observed in the size of the nanogel. This indicates that swelling of the nanogel is indeed due to pH variation.

To experiment the release of the encapsulated cargo in response to pH change, acid α-glucosidase (GAA) was encapsulated within the nanogel network using the same procedure described herein. Phosphate buffer solution of GAA (10 mg/mL) in the inverse microemulsion polymerization was used to generate the protein-encapsulated nanogel. To evaluate the concentration of GAA in the nanogel solution, a BCA (bicinconinic acid) assay (FIG. 7) was performed,[48] which revealed 28 μg of protein per mg of nanogel. (BCA assay is a standard assay for determination of protein concentration in an unknown solution. For details information see supporting information (FIG. 8).) The encapsulation efficiency of the nanogel was found to be ~90%. The rather high encapsulation efficiency is likely due to fact that the monomer, crosslinker, initiator, and protein are all hydrophilic and therefore would preferably remain inside the inverse micelle formed by Brij L4 surfactant prior to polymerization.

The activity of the encapsulated GAA, relative to the free GAA, was evaluated. It was envisioned that the enzyme would be less available to the substrate, when encapsulated, and therefore would have a lower activity. It follows then that the activity will be recovered when exposing the nanogel to lower pH, as the enzyme will be released in response to the β-thioester cleavage based decrosslinking. The enzymatic activity was measured using para-nitrophenol-α-D-glucopyranoside as substrate, the GAA-assisted cleavage of the α-1,4-linkage of which releases the chromophore p-nitrophenolate (pNP). At pH 7.4, the enzyme-containing nanogel did not exhibit any enzymatic activity. Note, however, that the enzymatic activity of GAA itself at pH 7.4 is undetectable (FIG. 4a).

To activate the GAA from the nanogel, the pH of the solution was reduced to 5.0 using acetate buffer. The activity of GAA dramatically increased (FIG. 4b). To calibrate the percentage of activity that was recovered after 48 hours of incubation at pH 5.0, the enzymatic activity of the GAA from the nanogel was compared with that of the free enzyme at the same concentration. About 75% of the enzymatic activity was recovered upon exposing the nanogel to lower pH and presumably releasing the enzyme from the nanogel (FIGS. 9, 10).

To confirm that the protein is indeed released from the nanogel network or the swelling of the decrosslinking nanogel causes the substrate to diffuse inside the nanogel, the DLS (FIG. 4c) was examined, as was the fluorescence (FIG. 11) of the GAA loaded nanogel before and after treatment in acidic conditions (pH≈5) over 48 h. DLS profile showed that the average hydrodynamic diameter of the GAA loaded nanogel at pH 7.4 is ~18 nm, which corroborate well with TEM data (FIG. 4d). However, the DLS profile of this nanogel changed after treating the nanogel in acidic condition (pH≈5.0). A bimodal distribution (FIG. 4c) was observed after the GAA-loaded nanogel was exposed to acidic pH; two distinct average hydrodynamic diameters of 24 nm and 90 nm were observed. These two radii presumably correspond to the released protein and to the swollen decrosslinked nanogel respectively. Slight increase in the size of the released GAA might be attributed to the aggregation of some protein over 48 h at room temperature. To confirm this, native GAA was incubated at pH 5.0 for 48 h and found similar increase in the size (FIG. 4c). This aggregation phenomenon could be the cause of ~25% loss of the enzymatic activity of the released GAA. In another control experiment, it was found that there was no change in the hydrodynamic diameter of the GAA loaded nanogel at pH 7.4 even after 10 days (FIG. 12). These results support the notion that the enzyme might be released upon decrosslinking in response to reduced pH. The DLS provides the supporting evidence that there might be a pH-induced decrosslinking and release of the enzyme.

To further test that (a) all the proteins used initially have encapsulated within the nanogel network and (b) the β-thiopropionate linker is responsible for the release of the encapsulated protein molecules, a control nanogel was designed and synthesized using a cross-linker which lacks β-thiopropionate functional group (FIG. 5a). In this case, the enzyme is not expected to be released from the nanogel at low pH. The structure of the control cross-linker is very similar to the pH-sensitive cross-linker, except the sulfur atom is replaced by a methylene unit in the cross-linker. The lack of β-thiopropionate functionality should render this nanogel insensitive to pH change. (Schoenmakers, et al. 2004 *J. Control. Release* 95, 291.) Encapsulation of GAA in this control nanogel was achieved using a method similar to the one above. The control nanogel's encapsulation efficiency is found to be ~50%, as assessed by the BCA. (Azagarsamy, et al. 2012 *Biomacromolecules* 13, 2219.) The lower encapsulation efficiency is likely due to the reduced hydrophilicity of the cross-linker (CC). (Barton, et al. 2000 *Polym Int.* 49, 358;) Nonetheless, the significant percentage of protein provides the opportunity to test our encapsulation and pH-induced decrosslinking/release hypotheses.

The time-dependent size change of the control nanogel was assessed by DLS at pH 5.0. Even after 48 h, no significant change in the hydrodynamic diameter of the nanogel was observed, suggesting that there is no decrosslinking mediated swelling (FIG. 5b). This feature was also reflected in the protein activity assay. Even after 48 h at pH 5.0, there was no significant enzymatic activity of the GAA (FIG. 5c). These observations suggest that: (i) the protein encapsulation in the nanogel turns off the enzymatic activity; (ii) GAA encapsulation through inverse emulsion polymerization places the enzyme inside the nanogel. If these were not present inside the nanogel, the unencapsulated enzyme would be active in the control nanogel experiments; and (iii) the β-thiopropionate linker is indeed responsible for the pH-sensitive decrosslinking/swelling and enzymatic activation.

Furthermore, since the nanogels are based on oligoethyleneglycol units as the surface functional groups and cross-linking moiety, it was important to acertain whether these nanogels are not cytotoxic. To test this, in vitro cell viability assay was carried out using an Alamar blue assay with 293T and MDA-MB-231 cell lines (FIG. 6). The cells were incubated with varying concentration of the nanogel solution for 24 h at 37° C. The nanogels exhibit >80% cell viability for both 293T and MDA-MB-231 cell lines in the entire concentration range. In addition to testing the cytotoxicity of the nanogels, it is also critical to investigate whether the degraded byproducts of the nanogels would be cytotoxic. Therefore, the cell viability of the degraded nanogel was also investigated at various concentrations. These too showed concentration-independent cell viability for both 293T and MDA-MB 231 cell lines (FIG. 13). These results are promising first steps to ultimately utilize these nanogels for in vivo applications.

Also disclosed herein is a unique non-cationic redox responsive nanogel platform for encapsulation of hydrophilic macromolecules including nuclei acids (e.g., DNA, RNA) and proteins (e.g., enzyme, antibodied, fragments thereof) has been developed.

These nanogels disassemble only in the presence of a redox stimulus to release the encapsulated hydrophilics. Here is an exemplary system having such capabilities:

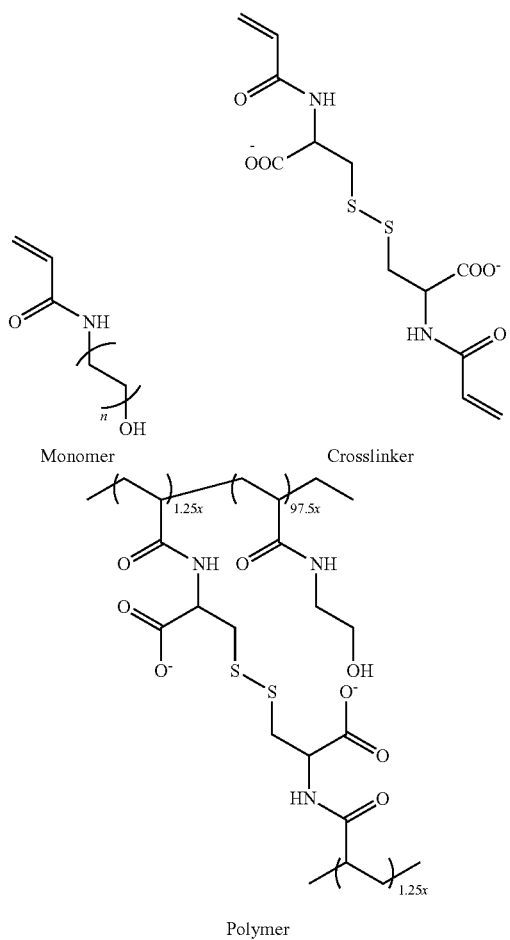

Employed here is the inverse emulsion strategy to achieve nanogels with a defined size. The nanogels are synthesized using acrylamide or acrylate based monomer and cross-linker, respectively. The redox responsive behavior of nanogels is achieved through cystine-modified crosslinker with a redox responsive unit. Both stable encapsulation of hydrophilic cargo in the nanogels and their disassembly and release upon treatment with reducing agent are demonstrated using gel electrophoresis and light scattering experiments, as disclosed herein.

Thus, the present disclosure demonstrates that (i) a hydrophilic biological cargo (e.g., enzyme or nucleid acid) can be conveniently encapsulated stably into a polymeric nanogel synthesized through the inverse microemulsion method; (ii) the cargo's biological activity is turned off when encapsulated within the nanogel; (iii) when the nanogel contains an acid-, base- or redox-labile or cross-linker, the nanogel can be decrosslinked in response to changes in pH or redox conditions; and (iv) the pH- or redox-induced decrosslinking event reversibly turns on the biological activity of the released.

Polymeric nanogel based biological delivery system disclosed herein can have profound implications in regard to therapeutical or diagnostic applications. The exemplary protein encapsulated disclosed herein, i.e. GAA, is involved in lysosomal storage diseases such as the Pompe disease. Since, the enzyme is turned off at the physiological pH of 7.4 and is then turned on at the lysosomal pH of 5, the method of reversibly turning off the enzymatic activity has biomedical implications.

EXPERIMENTAL SECTION

Materials

All the reagents were purchased from commercial source and used as such without further purification. $^1$H NMR spectra were recorded on a Bruker DPX-400 MHz NMR spectrometer and all the spectra were calibrated against TMS. Dynamic Light Scattering (DLS) measurements were carried out on a Malvern Nanozetasizer. TEM images were recorded on a JEOL-2000FX machine operating at an accelerating voltage of 100 KV. Fluorescence emission spectra were recorded on a Photon Technology International Quanta Master fluorometer. Mass spectrometric data were acquired by an electron spray ionization (ESI) technique on a Q-tof-micro quadruple mass spectrometer (Micro mass). Absorbance of para nitophenol was measured using a plate reader (SpectraMax M5). The enzyme acid alpha glucosidase (GAA) was provided as Myozyme, which was manufactured by Genzyme, Inc. of Cambridge, Mass. The GAA was stored as a lyophilized cake at 5° C. until reconstitution with MilliQ H$_2$O. The lyophilized formulation contained 5 mg/mL GAA, 25 mM Sodium Phosphate, 2% Mannitol, and 0.005% Tween-80 at pH 6.2 and was reconstituted to twice its original API and excipient concentration. Following reconstitution, the solution was stored as frozen aliquots at −80° C. until use.

Example 1 pH-responsive Release Polymer Nanogels

Synthesis of Nanogel

A monomer and cross-linker molar ratios of 95:5 was used. Monomer M and cross-linker C were taken in a vial and was diluted with 100 µL of initiator (I) solution (5.5 mg/mL) prepared with PBS buffer (10 mM, pH=7.4). The vial was then vortexed for 2 minutes to make it a homogeneous mixture. Inverse microemulsion (prepared separately) consisted of 5 mL heptanes and Brij L4 surfactant (0.60 g). The microemulsion was added to the vial containing M, C, I and was then subjected to vortex (5 minutes) followed by sonication (5 minutes). The reaction mixture was purged with argon gas for 10 minutes to remove oxygen. Finally, the reaction vessel was placed inside UV Chamber and exposed to UV light with mild stirring for 20 minutes. After the polymerization, it was diluted with measured volume of PBS buffer (pH=7.4) followed by addition of ~2 ml n-butanol. It was centrifuged for 15 min at 4400 rpm to remove all the surfactant and organic solvent. This was repeated twice to make sure all of the surfactants were removed. The resulting aqueous solution was dialyzed (MWCO 7000 Da) against PBS buffer for 24 h at 5° C. while water was changed in every 6 h.

Synthesis of GAA Loaded Nanogel

For the synthesis of acid degradable nanogel following inverse microemulsion polymerization process we have used monomer (150 mg, 0.604 mM) and cross-linker (18 mg, 0.03 mM) in the molar ratios of 95:5. Monomer M and cross-linker C were taken in a vial and was diluted with 100 µL of initiator (I) solution (5.5 mg/mL) prepared with PBS buffer (10 mM, pH=7.4). Then, 2 mg protein (acid alpha-glucosidase) was added to the mixture. The vial was then vortexed for 2 minutes to make it a homogeneous mixture. In separate vial inverse microemulsion was prepared using 5 mL of heptanes and 0.60 g of Brij L4 surfactant. The microemulsion was added to the vial containing M, C, I and protein and was then subjected to vortex (5 minutes) followed by sonication (5 minutes). The reaction mixture was purged with argon gas for 10 minutes to remove oxygen. Finally, the reaction vessel was placed inside UV Chamber and exposed to UV light with mild stirring for 20 minutes. After the polymerization, it was diluted with measured volume of PBS buffer (pH=7.4) followed by addition of ~2 ml n-butanol. It was centrifuged for 15 min at 4400 rpm to remove all the surfactant and organic solvent. This was repeated twice to make sure all of the surfactants were removed. The resulting aqueous solution was dialyzed (MWCO 7000 Da) against PBS buffer for 24 h at 5° C. while water was changed in every 6 h.

Synthesis of GAA Loaded Control Nanogel

Control nanogel has been synthesized using similar procedure stated above. In this case, we have used control cross-linker (CC) instead of cross-linker (C) and also monomer to cross-linker molar ratio was maintained to 95:5.

Dynamic Light Scattering (DLS) Study

For the DLS measurements concentration of the nanogel was 1 mg/mL. The solution was filtered using hydrophilic membrane (pore size 0.450 µm) before experiment was performed.

Transmission Electron Microscope (TEM) Study

For the TEM measurements the nanogel solution was prepared in 1 mg/ml concentration. One drop of the sample was dropcasted on carbon coated Cu grid. About 3 minutes after the deposition, the grid was tapped with filter paper to remove surface water.

Photoluminescence Study

Fluorescence spectroscopy was performed on a Photon Technology International Quanta Master fluorometer. GAA samples were diluted to 1 µM in 10 mM Acetate or 10 mM PBS buffer at pH 5.0 and 7.4, respectively. Tryptophans were excited at 295 nm (slit width 1 nm) and emission was monitored from 305-400 nm (slit width 3 nm) at 20° C. Five scans were performed on each sample and averaged. A blank buffer spectrum was collected for each buffering system and subtracted from the results prior to analysis. Data collection was handled by Felix32 software.

BCA Assay for Quantification of the Protein

At first calibration curve has been generated for known concentration of the protein using BCA assay kit. In the same way absorbance (@ 562 nm) of the unknown protein solution has been taken using plate reader. The absorbance value of the unknown protein solution was fitted in the calibration curve to get the protein concentration.

GAA Activity Assay

GAA activity was measured using para-nitrophenol-α-D-glucopyranoside as a substrate in 100 mM Citrate/100 mM Sodium Phosphate buffer at pH 5.0. The enzyme was incubated with the pre-warmed substrate at 37° C. in a Bio-Rad C1000 thermocycler. Aliquots were removed from the assay tubes and then quenched in 200 mM Borate buffer at pH 9.0 in a clear-bottom 96-well plate. Presence of the product formation (para-nitrophenolate) was then measured by absorbance of 400 nm light on a Molecular Devices Spectra Max M5 at 25° C. Final product concentrations were corrected for dilution factor and converted to molar concentrations using the known extinction coefficient.

Cell Viability

The in vitro cellular viability of the nanogels and the degraded nanogels were evaluated on healthy 293T and MDA-MB-231 breast cancer cell lines. The cells were cultured in T75 cell culture flasks using Dulbecco's Modified Eagle Medium/Nutrient Mixture F-12 (DMEM/F12) with 10% fetal bovine serum (FBS) supplement. The cells were seeded at 10,000 cells/well/200 µL in a 96 well plate and allowed to grow for 24 h under incubation at 37° C. and 5% CO2. These cells were then treated with nanogels of different concentrations and were incubated for another 24 hours. Cell viability was measured using the Alamar Blue assay with each data point measured in triplicate. Fluorescence measurements were made using the plate reader SpectraMax M5 by setting the excitation wavelength at 560 nm and monitoring emission at 590 nm on a black well plate.

Synthesis of the Monomer, Crosslinker and Control Crosslinker

Scheme 2 i)

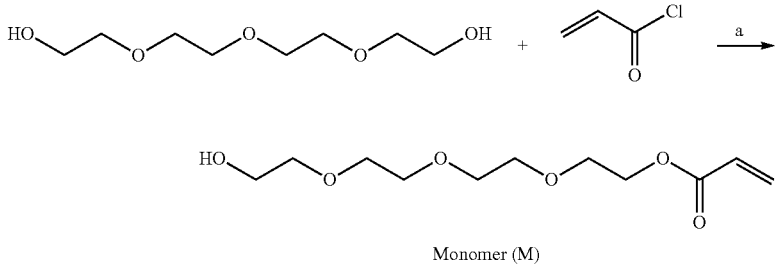

Monomer (M)

-continued ii)

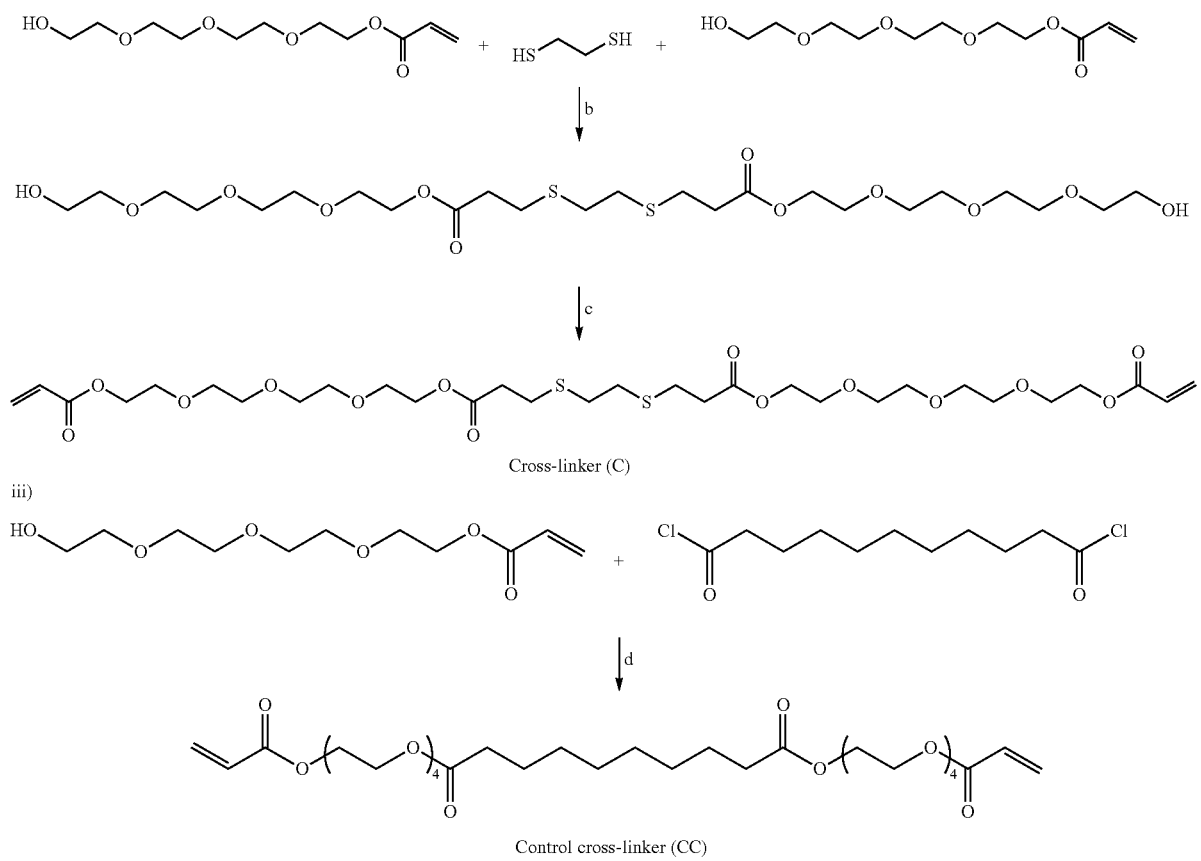

Cross-linker (C)

iii)

Control cross-linker (CC)

Reagents and Conditions: a) Et$_3$N, DCM, 0° C.-rt, 12 h; b) THF, Me$_2$PPh, rt, 24 h; c) Acryloyl Chloride, DCM, Et$_3$N, 0° C.-rt, 12 h; d) Et$_3$N, DCM, 0° C.-rt, 12 h.

i) Synthesis of Monomer (M): Monomer was synthesized following a literature reported procedure. (Dan, K.; Pan, R.; Ghosh, S. *Langmuir* 2011, 27, 612-617.)

$^1$H-NMR (400 MHz, CDCl$_3$, TMS): δ (ppm)=6.46 (d, 1H), 6.17 (m, 1H), 5.86 (d, 1H) 4.34 (t, 2H), 3.67 (m, 14H). HRMS (ESI): m/z calculated for C$_{11}$H$_{21}$O$_6$ (M+H)$^+$=249.1340, found 249.1350.

ii) Synthesis of Crosslinker (C), Step 1: 170 mg (1.80 mmol) of ethane dithiol and 980 mg (3.94 mmol) of tetra ethylene glycol acrylate monomer were taken in a round bottom flask along with 15 mL dry THF. Catalytic amount of dimethyl-phenylphosphine (6 mg, 0.044 mmol) was added to the reaction mixture and it was stirred for 24 h at room temperature under Argon atmosphere. The reaction was stopped and solvent was evaporated to get crude product as oil. It was purified by column chromatography using silica gel as stationary phase and hexane/Ethylacetate as eluent. Finally, pure product was separated as light yellow oil in 75% yield.

$^1$H-NMR (400 MHz, CDCl$_3$, TMS): δ (ppm)=4.30 (t, 4H), 3.75-3.62 (m, 28H), 2.84 (t, 4H), 2.76 (s, 4H), 2.67 (t, 4H). HRMS (ESI): m/z calculated for C$_{24}$H$_{47}$O$_{12}$S$_2$ (M+H)$^+$=591.2511, found 591.2510.

Synthesis of Crosslinker (C), Step 2: 650 mg (1.1 mmol) of the product obtained in the previous step and 15 mL dry CH$_2$Cl$_2$ was taken in a round bottom flask. To this solution 394 mg (3.9 mmol) triethylamine was added and the reaction mixture was stirred in an ice bath. To the reaction mixture a solution of acryloyl chloride (471 mg, 5.2 mmol) in 10 mL dry CH$_2$Cl$_2$ was added drop-wise with constant stirring under Argon atmosphere. After the addition was over the reaction mixture was stirred at room temperature for 12 h. The reaction was stopped and the solution was washed with H$_2$O (2×50 mL) to remove triethyl amine hydrochloride salt and the unreacted acryloyl chloride which has been converted to acrylic acid in presence of water. The combined organic part was dried over anhydrous Na$_2$SO$_4$ and CH$_2$Cl$_2$ was removed under reduced pressure to get the crude product as brown color oil. For the complete removal of acrylic acid, the crude product was kept under vacuum for 24 h to get pure product as brown color semisolid in quantitative yield.

$^1$H-NMR (400 MHz, CDCl$_3$, TMS): δ (ppm)=6.46 (d, 2H), 6.17 (m, 2H), 5.86 (d, 2H) 4.33-4.27 (m, 8H), 3.77-3.67 (m, 24H), 2.84 (t, 4H), 2.76 (s, 4H), 2.66 (t, 4H). $^{13}$C (CDCl$_3$) δ (ppm): 171.78, 166.16, 131.03, 128.28, 70.63, 70.58, 69.13, 69.07, 63.85, 63.67, 34.78, 32.11, and 26.98. HRMS (ESI): m/z calculated for C$_{30}$H$_{50}$O$_4$S$_2$Na (M+Na)$^+$=721.2540, found 721.2517.

iii) Synthesis of Control Crosslinker (CC): 550 mg (2.21 mmol) of monomer, M and 253 mg (2.5 mmol) triethylamine were dissolved in 10 ml dry CH$_2$Cl$_2$ in a round bottom flask. The reaction mixture was stirred and cooled in an ice bath. Sebacoyl chloride (241 mg, 1.007 mmol) was dissolved in dry CH$_2$Cl$_2$ and was added drop wise to the cold solution of monomer and triethylamine mixture under argon atmosphere. After the addition was over reaction was carried out for another 12 h at room temperature. The reaction was stopped and the mixture was washed with $H_2O$ (2×50 mL) to remove the triethylamine hydrochloride salt and the aqueous phase were treated with dichloromethane (2×30 mL) to extract the crude product. The combined organic layer was dried over anhydrous $Na_2SO_4$ and $CH_2Cl_2$ was removed under reduced pressure to get the crude product as colorless oil. It was purified by column chromatography using silica gel as stationary phase and ethylacetate/hexane as eluent. The pure product was separated as colorless oil in 50% yield.

$^1H$ NMR (300 MHz, $CDCl_3$, TMS): δ (ppm)=6.46 (d, 2H), 6.17 (m, 2H), 5.86 (d, 2H) 4.33 (t, 4H), 4.23 (t, 4H), 3.76-3.66 (m, 24H), 2.33 (t, 4H), 1.62 (t, 4H), 1.3 (m, 8H). $^{13}C$ ($CDCl_3$) δ (ppm): 173.76, 166.14, 131.00, 128.28, 70.64, 70.57, 69.21, 69.13, 63.67, 63.35, 34.16, 29.08, 29.06, and 24.85. HRMS (ESI): m/z calculated for $C_{32}H_{54}O_{14}Na$ $(M+Na)^+$=685.3412, found 685.3412.

Example 2 pH-responsive Release Polymer Nanogels

Synthesis of Nanogels

Brij L4 (0.3 mg) was dissolved in heptane (2.5 g) and mixed well by vortex to obtain a clear solution. To this solution 0.408 mmoles of hydroxyl ethyl acrylamide (HEA) and 0.010 mmoles of crosslinker cystine diacrylamide is added along with 10 mg of ammonium persulfate initiator (APS) were added along with the hydrophilic cargo. In this study 10 µg of GFP plasmid/Protein/dsRNA was added, the total amount of PBS used to dissolve all the monomer was about 200 µL and vortexed until a clear solution is obtained, it is then sonicated in a bath sonicator for 2 minutes. Then the emulsion solution is purged with argon for 5 minutes to remove any dissolved oxygen. To this solution 25 µL of tertamethylethylenediamine (TEMED) is added and stirred for 30 minutes.

Extraction of Nanogels

After the crosslinking reaction, 8 mL of phosphate buffer saline was added to the inverse emulsion solution along with 2 mL butanol and stirred for 5 minutes and then centrifuged for 15 minutes under 5000 rpm. The organic layer was then discarded and then the water layer was collected for the nanogels. To remove any unreacted monomers and surfactant, it was dialysed using 7000 MWCO dialysis membrane for 48 hours at 4° C. with two water changes. After dialysis the dry weight of the nanogel solution is calculated to estimate the concentration of the solution.

Redox Responsive Behavior of GFP Plasmid Encapsulated Nanogels

Dynamic light scattering (DSL) analysis was used to observe the size change of nanogels before and after treatment with reducing agent (FIG. 19). Nanogels without reducing environment did not show a plasmid band and has intact nanogel with plasmid in the well. Nanogel treated with reducing environment shows a plasmid band and also reduced nanogel amount in the well. These were confirmed by agarose gel electrophoresis assay (FIG. 20).

Redox Responsive Behavior of dsRNA Encapsulated Nanogels

To study the redox responsive behavior of plasmid encapsulated nanogels DLS analysis was used to measure the size change of nanogels before and after treatment with reducing agent (FIG. 21). As shown in FIG. 22, agarose gel electrophoresis assay demonstrated the redox responsive behavior of dsRNA-encapsulated nanogels. Nanogels without reducing environment did not show a RNA band and has intact nanogel with RNA in the well. Nanogel treated with reducing environment shows a RNA band and also reduced nanogel amount in the well. FIG. 23 shows the redox responsive behavior of ds RNA encapsulated nanogels upon responding to different concentrations of reducing agent.

Redox Responsive Behavior of Protein Encapsulated Nanogels

Studies were also conducted for protein encapsulation and redox-responsive release. FIG. 24 shows DSL analysis of the size change of nanogels before and after treatment with reducing agent. FIG. 25 SDS gel electrophoresis assay was performed to show the redox responsive behavior of protein encapsulated nanogels. Nanogels without reducing environment did not show a protein band whereas nanogel treated with reducing environment shows a protein band In this specification and the appended claims, the singular forms "a," "an," and "the" include plural reference, unless the context clearly dictates otherwise. Unless defined otherwise, all technical and scientific terms used herein have the same meaning as commonly understood too one of ordinary skill in the art. Unless defined otherwise, all technical and scientific terms used herein have the same meaning as commonly understood by one of ordinary skill in the art. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

The invention claimed is:

1. A crosslinked polymeric nanogel, adapted to stably encapsulate a hydrophilic biomolecule at a first pH condition and then release it at a second pH condition, wherein the crosslinked polymeric nanogel is crosslinked with an acid-labile crosslinker and comprises the structural unit:

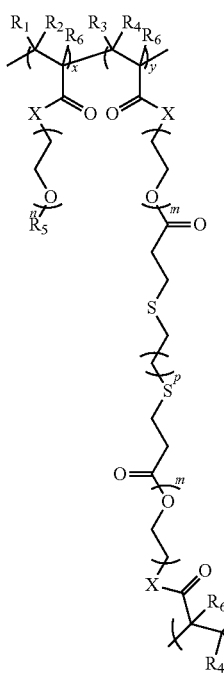

wherein
- each of $R_1$, $R_2$, $R_3$, $R_4$, $R_5$ and $R_6$ is independently a hydrogen, $C_1$-$C_{12}$ alkyl group, or halogen;
- each of x and y is independently a positive number;
- each of m and p is independently an integer from about 1 to about 10;
- n is a positive number from 1 to about 200; and
- X is independently chosen from O and NH.

2. The crosslinked polymeric nanogel of claim 1, wherein each of $R_1$, $R_2$, $R_3$, $R_4$, $R_5$ and $R_6$ is a hydrogen.

3. The crosslinked polymeric nanogel of claim 1, wherein the second pH is lower than the first pH.

4. The crosslinked polymeric nanogel of claim 3, wherein the second pH is from about 3.5 to about 6.4 and the first pH is from about 6.5 to about 8.0.

5. A crosslinked polymeric nanogel, adapted to stably encapsulate a hydrophilic biomolecule at a first redox condition and then release it at a second redox condition, wherein the crosslinked polymeric nanogel is crosslinked with a redox-labile crosslinker and comprises the structural unit:

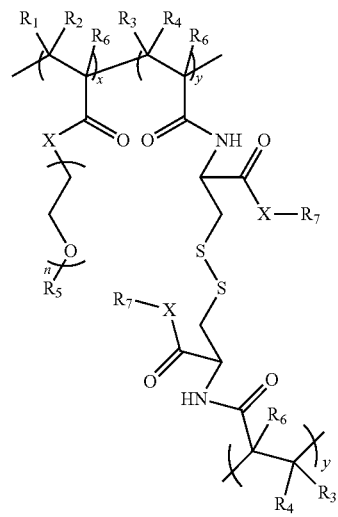

wherein
- each of $R_1$, $R_2$, $R_3$ $R_4$, $R_5$ and $R_6$ is independently a hydrogen, $C_1$-$C_{12}$ alkyl group, or halogen;
- $R_7$ is independently a hydrogen, $C_1$-$C_{12}$ alkyl group, or an ethyleneglycol chain with 2 to about 200 repeat units;
- each of x and y is independently a positive number;
- n is a positive number from 1 to about 200; and
- X is independently chosen from O or NH.

6. The crosslinked polymeric nanogel of claim 5, wherein each of $R_1$, $R_2$, $R_3$, $R_4$, $R_5$ and $R_6$ is a hydrogen.

7. The crosslinked polymeric nanogel of claim 5, wherein the redox-labile crosslinker comprises one or more moieties selected from acrylate, methacrylate or a disulfide moiety.

* * * * *